United States Patent
Miura et al.

(10) Patent No.: US 10,639,162 B2
(45) Date of Patent: May 5, 2020

(54) ARTIFICIAL KNEE JOINT

(71) Applicant: National University Corporation Ehime University, Ehime (JP)

(72) Inventors: Hiromasa Miura, Ehime (JP); Kazunori Hino, Ehime (JP)

(73) Assignee: NATIONAL UNIVERSITY CORPORATION EHIME UNIVERSITY, Ehime (JP)

( * ) Notice: Subject to any disclaimer, the term of this patent is extended or adjusted under 35 U.S.C. 154(b) by 0 days.

(21) Appl. No.: 15/321,912

(22) PCT Filed: Jun. 24, 2015

(86) PCT No.: PCT/JP2015/068237
§ 371 (c)(1),
(2) Date: Dec. 23, 2016

(87) PCT Pub. No.: WO2015/199143
PCT Pub. Date: Dec. 30, 2015

(65) Prior Publication Data
US 2017/0156871 A1 Jun. 8, 2017

(30) Foreign Application Priority Data

Jun. 24, 2014 (JP) ................................ 2014-128832

(51) Int. Cl.
*A61F 2/38* (2006.01)
*A61F 2/30* (2006.01)

(52) U.S. Cl.
CPC ................ *A61F 2/385* (2013.01); *A61F 2/38* (2013.01); *A61F 2/389* (2013.01); *A61F 2/3859* (2013.01);
(Continued)

(58) Field of Classification Search
CPC ........ A61F 2/389; A61F 2/3868; A61F 2/385; A61F 2002/30688
See application file for complete search history.

(56) References Cited

U.S. PATENT DOCUMENTS 5,080,675 A * 1/1992 Lawes ................... A61F 2/3868
623/20.3
5,358,527 A * 10/1994 Forte ..................... A61F 2/3845
623/20.27
(Continued)

FOREIGN PATENT DOCUMENTS

CN 102481187 A 5/2012
JP 2003-501205 A 1/2003
(Continued)

OTHER PUBLICATIONS

Office Action dated Jan. 6, 2020 received in corresponding Chinese application No. 201580033461.1, (11 pages) and English translation (15 pages).

*Primary Examiner* — Bruce E Snow
*Assistant Examiner* — Melissa A Hoban
(74) *Attorney, Agent, or Firm* — Foley & Lardner LLP

(57) ABSTRACT

The present invention provides an artificial knee joint that can reconstruct an anterior cruciate ligament in a state close to an original function. An artificial knee joint (1) that is used in a total knee replacement includes a femur member (10) and a tibia member (20). The tibia member (20) has a ligament insertion hole (20*h*) which pierces the tibia member (20) and which is formed at a position where once an anterior cruciate ligament (ACL) exists in a knee replaced for the artificial knee joint (1). Therefore, a ligament can be provided such that a distal end (DT) of a femur (F) and a proximal end (PE) of a tibia (T) are joined to each other by passing the ligament through the ligament insertion hole (20*h*), which allows the anterior cruciate ligament (ACL) to (Continued)

be reconstructed so as to be in the substantially same state as a knee replaced for the artificial knee joint (1).

12 Claims, 38 Drawing Sheets

(52) U.S. Cl.
CPC .. *A61F 2/3886* (2013.01); *A61F 2002/30688* (2013.01); *A61F 2002/30772* (2013.01)

(56) References Cited

U.S. PATENT DOCUMENTS

| | | | |
|---|---|---|---|
| 6,679,914 B1 | 1/2004 | Gabbay | |
| 6,755,864 B1 | 6/2004 | Brack et al. | |
| 6,905,513 B1* | 6/2005 | Metzger | A61F 2/08 623/20.14 |
| 7,153,327 B1* | 12/2006 | Metzger | A61F 2/08 623/20.29 |
| 8,480,754 B2 | 7/2013 | Bojarski et al. | |
| 8,906,107 B2 | 12/2014 | Bojarski et al. | |
| 8,926,706 B2 | 1/2015 | Bojarski et al. | |
| 8,974,539 B2 | 3/2015 | Bojarski et al. | |
| 2002/0058997 A1 | 5/2002 | O'Connor et al. | |
| 2002/0156535 A1* | 10/2002 | Pappas | A61F 2/3868 623/20.29 |
| 2009/0306783 A1 | 12/2009 | Blum | |
| 2009/0306784 A1 | 12/2009 | Blum | |
| 2010/0286788 A1 | 11/2010 | Komistek | |
| 2010/0298894 A1 | 11/2010 | Bojarski et al. | |
| 2011/0029093 A1 | 2/2011 | Bojarski et al. | |
| 2011/0106265 A1 | 5/2011 | Wolfson et al. | |
| 2011/0190898 A1 | 8/2011 | Lenz et al. | |
| 2012/0022660 A1* | 1/2012 | Wentorf | A61F 2/389 623/20.32 |
| 2012/0191205 A1 | 7/2012 | Bojarski et al. | |
| 2012/0191420 A1 | 7/2012 | Bojarski et al. | |
| 2012/0232669 A1 | 9/2012 | Bojarski et al. | |
| 2012/0232670 A1 | 9/2012 | Bojarski et al. | |
| 2012/0232671 A1 | 9/2012 | Bojarski et al. | |
| 2015/0018960 A1 | 1/2015 | El Zoghbi et al. | |
| 2015/0081029 A1 | 3/2015 | Bojarski et al. | |

FOREIGN PATENT DOCUMENTS

| | | |
|---|---|---|
| JP | 2004-513698 A | 5/2004 |
| JP | 4195177 B2 | 10/2008 |
| JP | 2011-502608 A | 1/2011 |
| JP | 2012-521789 A | 9/2012 |
| JP | 2012-523897 A | 10/2012 |
| JP | 2012-531265 A | 12/2012 |
| JP | 2013-517911 A | 5/2013 |
| JP | 2013-172992 A | 9/2013 |
| JP | 2013-215456 A | 10/2013 |
| JP | 2015-515325 A | 5/2015 |
| WO | WO 00/76428 A1 | 12/2000 |
| WO | WO 02/39889 A2 | 5/2002 |
| WO | WO 2009/056836 A2 | 5/2009 |
| WO | WO 2009/148689 A1 | 12/2009 |
| WO | WO 2010/108550 A1 | 9/2010 |
| WO | WO-2010/120520 A2 | 10/2010 |
| WO | WO 2010/121147 A1 | 10/2010 |
| WO | WO 2010/151564 A1 | 12/2010 |
| WO | WO 2011/094540 A2 | 8/2011 |
| WO | WO 2013/152341 A1 | 10/2013 |

* cited by examiner

ARTIFICIAL KNEE JOINT

TECHNICAL FIELD

The present invention relates to an artificial knee joint.

BACKGROUND ART

A knee joint is a joint that is constructed with a femur, a tibia, and a kneepan. A knee cartilage or a meniscus is located between a distal end of the femur and a proximal end of the tibia, and acts as a cushion in the knee joint, whereby the knee joint can smoothly work.

However, when the knee cartilage or the meniscus is worn off due to fatness or aging, not only a cushioning property between the distal end of the femur and the proximal end of the tibia is lost, but also the knee joint is possibly deformed. The knee joint is deformed when joint rheumatism is gotten, or when the knee is injured. For the deformation (knee osteoarthritis) of the knee joint, the knee joint cannot smoothly work, but a patient feels a bad pain in walking, and sometimes the patient has difficulty walking.

A total knee replacement is adopted as a treatment technique for the knee osteoarthritis. In the total knee replacement, the distal end of the femur and the proximal end of the tibia are cut off, and the cut portion is replaced with the artificial knee joint. Currently many patients are subjected to the total knee replacement, which allows relief of the pain or performance of the normal walking. Therefore, many patients highly satisfy the total knee replacement. There have been developed many artificial knee joints used in the total knee replacement (see Patent Documents 1 and 2).

In the knee joint, the femur and the tibia are joined to each other by a ligament in order to stabilize the working and attitude of the knee joint. However, sometimes the ligament joined to the distal end of the femur and the proximal end of the tibia, namely, an anterior cruciate ligament or a posterior cruciate ligament is cut off because the distal end of the femur and the proximal end of the tibia are cut off in performing the total knee replacement. Currently there are two methods, namely, a method (see Patent Document 1) in which both the cruciate ligaments are cut off to substitute a ligament function for the artificial knee joint and a method (see Patent Document 2) in which the anterior cruciate ligament is cut off while the posterior cruciate ligament is preserved. The method to be adopted is selected according to a damaged condition of the joint or ligament.

The anterior cruciate ligament is removed in both the methods. Although the artificial knee joint can be substituted for the function of the anterior cruciate ligament, the artificial knee joint is far inferior to the function of the original anterior cruciate ligament. Therefore, a patient having the artificial knee joint does not feel inconvenience in normal walking too much, but feels inconvenience when going up and down the stairs.

A patient having the artificial knee joint due to an injury of sports has a strong demand to do sports even if having the artificial knee joint. However the above methods cannot respond to the demand.

An artificial knee joint having a form of preserving the anterior cruciate ligament is also developed in order to respond to the demand (Patent Document 3). However, the anterior cruciate ligament is frequently damaged in the knee osteoarthritis, and sometimes a ligament length changes in association with the joint deformation. In the artificial knee joint of Patent Document 3, even if the anterior cruciate ligament is preserved, the anterior cruciate ligament hardly exerts the sufficient function. In the knee osteoarthritis caused by the damaged anterior cruciate ligament, even if the anterior cruciate ligament is preserved, the function of the anterior cruciate ligament can hardly be expected to be exerted.

Patent Document 4 discloses a technique of joining a femur member and a tibia member to each other by an artificial ligament as a mechanism preventing mobilization of an insert in an artificial knee joint including the tibia member and an insert mobile mechanism (a mechanism in which the insert moves on the tibia member with a freedom degree). In the technique of Patent Document 4, an end of a tibia-side member of the artificial ligament is joined to tibia-side member with an elastic member such as a spring interposed therebetween, which allows hardness of the artificial ligament to be brought close to natural hardness.

PRIOR ART DOCUMENTS

Patent Documents

Patent Document 1: JP 2013-172992 A
Patent Document 2: Japanese Patent No. 4195177
Patent Document 3: JP 2013-517911 T
Patent Document 4: JP 2011-502608 T
Patent Document 5: JP 2013-215456 A

DISCLOSURE OF THE INVENTION

Problems to be Solved by the Invention

In the technique of Patent Document 4, a function of connecting the femur member and the tibia member to each other exists because the artificial ligament is provided between the femur member and the tibia member. The artificial knee joint members are joined to each other, but the femur and the tibia are not directly joined to each other. Accordingly, when tractive force is generated between the femur member and the tibia member, there is a risk of breaking the ligament or loosening the artificial joint. Therefore, it is difficult to sufficiently exert the function of the anterior cruciate ligament in the original knee joint.

In order to provide the artificial knee joint to return to the state of the original knee joint, it is necessary to reconstruct the anterior cruciate ligament. However, in the technique of Patent Document 4, the artificial ligament is provided as only a part of the configuration of the artificial knee joint, but the reconstruction of the anterior cruciate ligament is not considered.

On the other hand, in Patent Document 5, the anterior cruciate ligament adhering part is preserved by cutting the tibia member into a U-shape. Additionally, a hole piercing the tibia member is formed, and a reconstruction anterior cruciate ligament is inserted in the hole, thereby fixing the reconstruction anterior cruciate ligament to the femur and the tibia. That is, Patent Document 5 discloses an artificial knee joint that can reconstruct the anterior cruciate ligament to join the femur and the tibia to each other.

However, in the description of Patent Document 5, making the hole facilitates production of a tibia component to improve strength. That is, in the description of Patent Document 5, the hole is formed based on an idea that the femur and the tibia are directly joined to each other by the reconstructed anterior cruciate ligament. However, there is no specific description about a position of the hole, and a relationship between a layout of the hole and the function of the reconstructed anterior cruciate ligament is not considered. The technique of Patent Document 5 gives no suggestion of the specific layout of the hole, which is necessary to exert the function of the reconstructed anterior cruciate ligament As described above, although various artificial knee joints are developed, artificial knee joint in which the function of the anterior cruciate ligament in the original knee joint can sufficiently be exerted is not developed yet. Therefore, there is a demand to develop the artificial knee joint in which the original function can sufficiently be exerted.

An object of the present invention is to provide an artificial knee joint that can reconstruct the anterior cruciate ligament in a state close to the original function.

Means for Solving the Problems

According to a first aspect, an artificial knee joint is used in a total knee replacement to join a femur and a tibia to each other using a reconstruction ligament formed by a plurality of bundles of reconstruction ligaments, and the artificial knee joint includes: a femur member mounted on a femur distal end; and a tibia member mounted on a tibia proximal end. At this point, a medial condyle and a lateral condyle are provided in the tibia member, the medial condyle and the lateral condyle of the tibia member being in contact with a medial condyle and a lateral condyle of the femur member, respectively, a ligament insertion hole piercing the tibia member and an intercondylar eminence are provided between the medial condyle and the lateral condyle of the tibia member, the ligament insertion hole is provided at a position where once an anterior cruciate ligament exists in a knee replaced for the artificial knee joint, the intercondylar eminence is formed between the ligament insertion hole and a notch provided in a rear portion of the tibia member, a height of the intercondylar eminence is substantially equal to a height of an intercondylar eminence in a knee replaced for the artificial knee joint, and a recess anteroposteriorly extending along the artificial knee joint is provided at a leading end of the intercondylar eminence such that an interference state changes in each bundle of reconstruction ligaments of a reconstruction anterior cruciate ligament when the knee is bent and stretched while replaced for the artificial knee joint to provide the reconstruction anterior cruciate ligament formed by the plural bundles of reconstruction ligaments.

According to a third aspect, in the artificial knee joint of the first aspect, the ligament insertion hole is provided such that a center of an opening is disposed at a position of 25% to 50% from a front end of the tibia member 20, and such that the center of the opening is disposed at a position of 0 to 10% from right to left from a center in right and left directions.

According to a fourth aspect, in the artificial knee joint of the first or third aspect, a plurality of the ligament insertion holes are provided such that a center of an opening of each hole is disposed at a position of 25% to 50% from a front end of the tibia member 20, and such that the center of the opening of each hole is disposed at a position of 0 to 10% from right to left from a center in right and left directions.

According to a fifth aspect, in the artificial knee joint of any one of the first, third, and fourth aspects, in the tibia member, a central portion of the medial condyle is formed into a concave surface, and a central portion of the lateral condyle is formed into a flat surface.

According to a sixth aspect, in the artificial knee joint of any one of the first, third, fourth, and fifth aspects, in the tibia member, a surface connecting a front end and a rear end of the concave surface in the central portion of the medial condyle is formed so as to tilt backward with respect to the flat surface in the central portion of the lateral condyle in a side view.

According to a seventh aspect, in the artificial knee joint of any one of the first, third, fourth, fifth, and sixth aspects, in the tibia member, a surface of the medial condyle tilts inward so as to be lower than a surface in the central portion of the lateral condyle in a rear view.

According to an eighth aspect, in the artificial knee joint of any one of the first, third, fourth, fifth, sixth, and seventh aspects, in the tibia member, peripheral portions of the medial condyle and/or the lateral condyle are formed into a curved shape.

According to a ninth aspect, in the artificial knee joint of the eighth aspect, in the tibia member, a boundary portion between a side surface and/or a rear surface and lateral condyle is formed into an outward convex surface.

Effect of the Invention

According to the first aspect, since, in the tibia member, the ligament insertion hole is provided at the position where once the anterior cruciate ligament exists in the knee replaced for the artificial knee joint, when the artificial ligament or organism ligament (hereinafter, simply referred to as a reconstruction ligament) is passed through the ligament insertion hole, the reconstruction ligament can be provided such that the distal end of the femur and the proximal end of the tibia are joined to each other. Additionally, the intercondylar eminence is provided between the ligament insertion hole and the notch provided in the rear portion of the tibia member. Therefore, in bending and stretching the knee, the reconstructed anterior cruciate ligament and the intercondylar eminence interfere with each other by providing the intercondylar eminence. This enables the reconstructed anterior cruciate ligament to generate the relaxation and tension states similar to those of the anterior cruciate ligament in the knee replaced for the artificial knee joint. Additionally, the reconstruction ligament is formed by the plurality of bundles of reconstruction ligaments, and the recess is provided at the leading end of the intercondylar eminence. Therefore, the interference state changes in each bundle of reconstruction ligaments when the reconstruction ligaments interfere with the leading end of the intercondylar eminence. That is, the tensile force generated in each bundle of reconstruction ligaments is adjusted so as to be in a proper state, so that the movement of the anterior cruciate ligament or the generated tensile force can be equalized to that of an anterior cruciate ligament of a human. Additionally, the femur and the tibia can be prevented from skidding by the intercondylar eminence. Accordingly, movement of the knee replaced for the artificial knee joint can be brought into the state closer to the original knee before the replacement for the artificial knee joint.

According to the third aspect, in bending and stretching the knee, a tensile force generated in the reconstructed anterior cruciate ligament and relaxation and tension states can be equalized to those of the anterior cruciate ligament in the knee replaced for the artificial knee joint.

According to the fourth aspect, each ligament constituting the reconstructed anterior cruciate ligament can be brought closer to the state of the original anterior cruciate ligament.

According to the fifth aspect, the medial condyle and the lateral condyle are formed into the shapes close to those of the organism tibia while the anterior cruciate ligament is in the reconstructed state, so that the movement of the artificial knee joint can be brought closer to the natural movement.

According to the sixth and seventh aspects, the shape of the tibia member is close to that of the tibia proximal end, so that the movement of the artificial knee joint can be brought closer to the natural movement.

According to the eighth aspect, even if the medial condyles of the femur member and the tibia member and/or the lateral condyles of the femur and the tibia member move relatively, a large load can be prevented from being applied to surrounding potions of the medial condyle and/or the lateral condyle of the tibia member. That is, edge loading can be reduced, and therefore the damage of the femur member and tibia member can be prevented.

According to the ninth aspect, since the edge loading can be reduced, the damage of the femur member and tibia member can be prevented. Additionally a movable range of the knee can be widened after the replacement for the artificial knee joint.

BRIEF DESCRIPTION OF THE DRAWINGS

FIG. 35 is a view illustrating an interference state between the anterior cruciate ligament and an intercondylar eminence.

MODE FOR CARRYING OUT THE INVENTION

Figure 1:
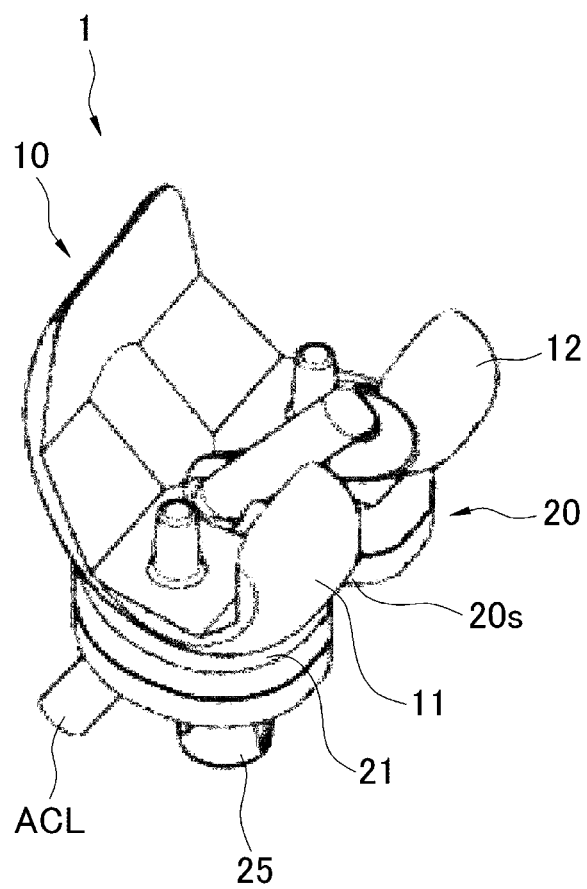
FIG. 1 is a perspective view schematically illustrating an artificial knee joint 1 according to an embodiment.
Figure 2A:
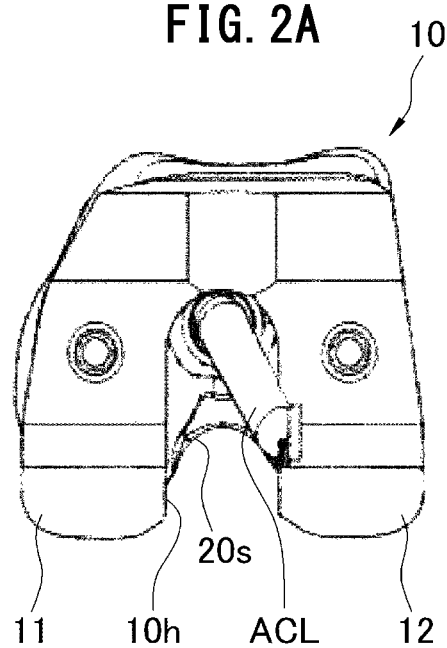
FIGS. 2(A) and 2(B) are plan and bottom views schematically illustrating the artificial knee joint 1 of the embodiment, respectively.
Figure 2B:
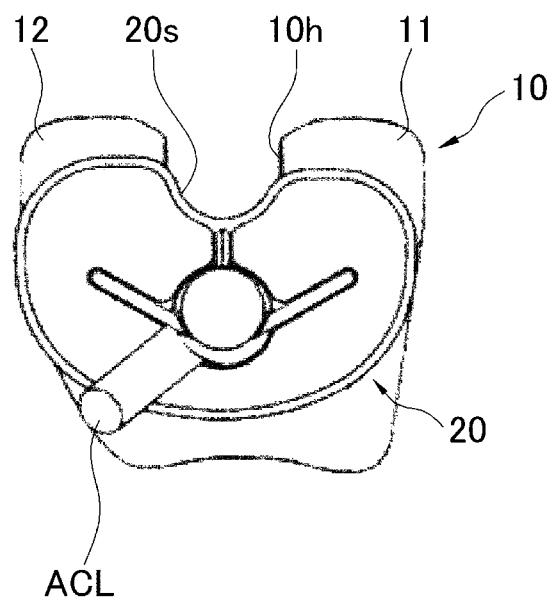
Figure 3A:
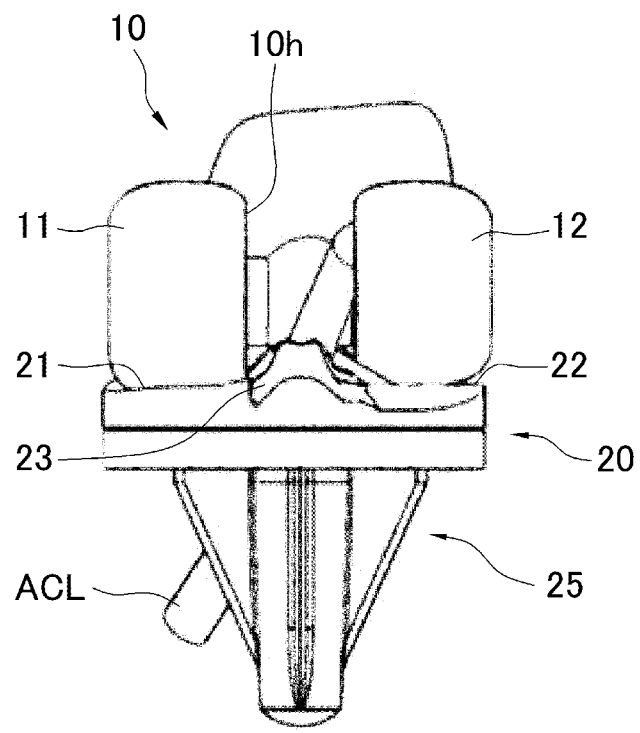
FIGS. 3(A) and 3(B) are rear and front views schematically illustrating the artificial knee joint 1 of the embodiment, respectively.
Figure 3B:
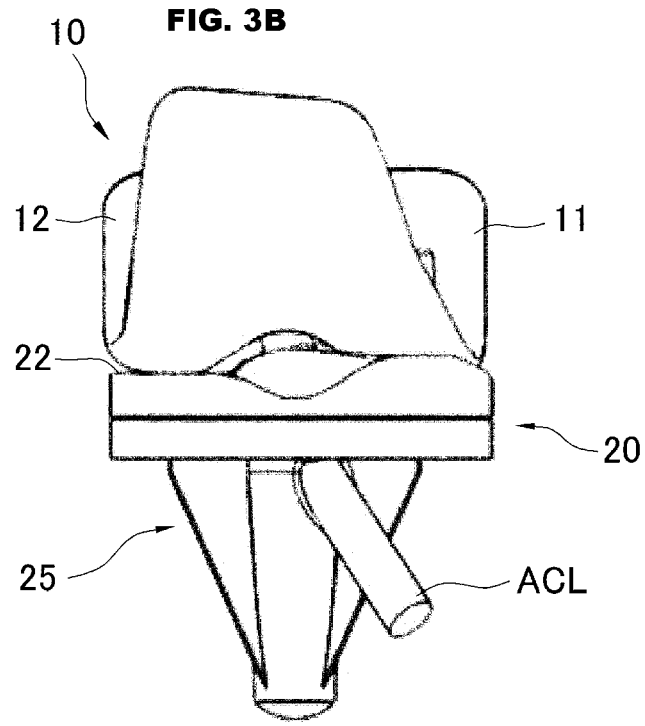
Figure 4A:
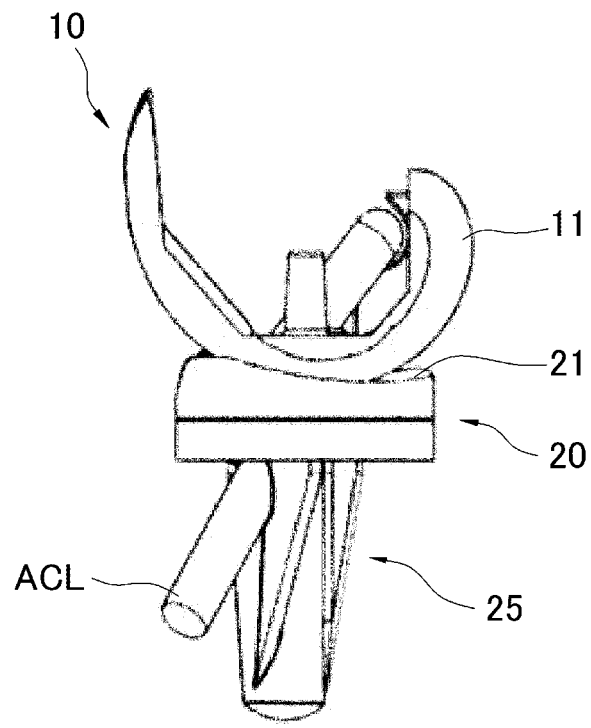
FIGS. 4(A) and 4(B) are right and left views schematically illustrating the artificial knee joint 1 of the embodiment, respectively.
Figure 4B:
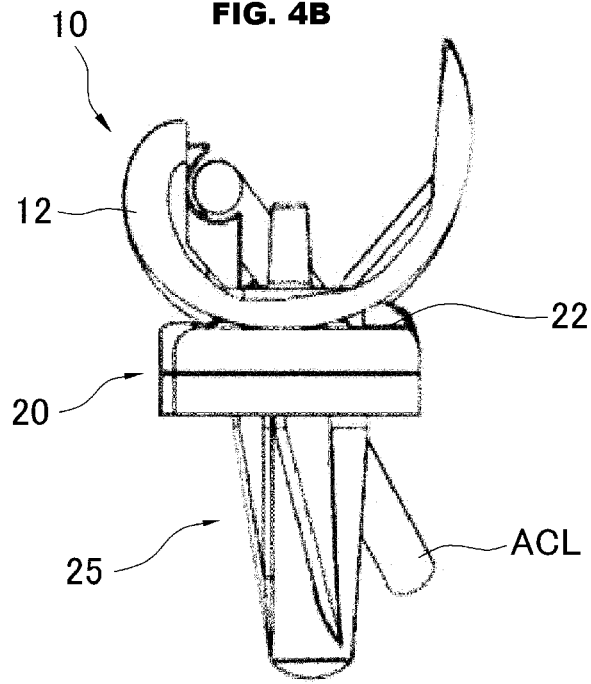

An artificial knee joint of the present invention is used in a total knee replacement in the treatment of the knee osteoarthritis, the joint rheumatism, or the like, and has a feature of a structure in which the anterior cruciate ligament can be reconstructed.

As used herein, the reconstruction of the anterior cruciate ligament means that the ligament constituting the anterior cruciate ligament is joined so as to be directly connected to not the artificial knee joint, but the femur and the tibia. That is, one of ends of the ligament constituting the anterior cruciate ligament is directly joined to the femur while the other end is directly joined to the tibia.

In the description, the ligament used to reconstruct the anterior cruciate ligament includes both the artificial ligament artificially formed with polyester and the like as a row material and an organism tendon (organism ligament) collected from another region of an organism. Hereinafter, the ligament including the artificial ligament and the organism tendon is referred to as a reconstruction ligament.

(Artificial Knee Joint 1 of the Embodiment)

As illustrated in FIGS. 1 to 7, an artificial knee joint 1 according to an embodiment includes a femur member 10 and a tibia member 20.

In FIGS. 1 to 7, the artificial knee joint 1 for a right knee is described as a representative. For clarification of the structure, a posterior cruciate ligament PCL is omitted in FIGS. 1 to 7, and a femur F and a tibia T are also omitted in FIGS. 1 to 4.

The tibia member 20 is formed by a combination of a base part 20a and a contact part 20b. The following description is made on the assumption that the contact part 20b is placed on and joined to a top surface of the base part 20a to combine the base part 20a and the contact part 20b with each other. That is, the description is made as if the tibia member 20 is made of one member.

(Femur Member 10)

Figure 5A:
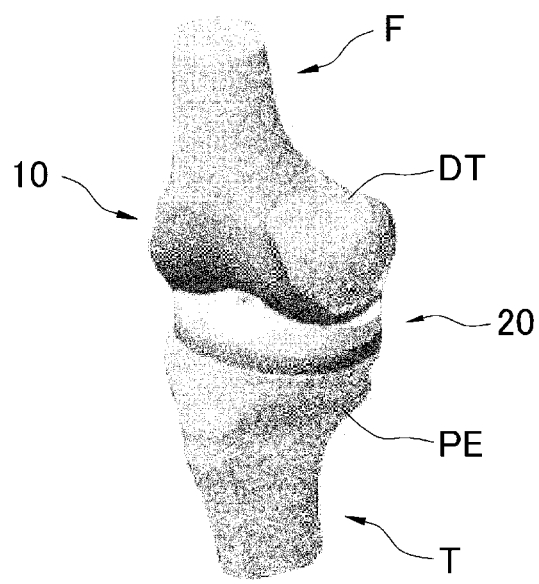
FIG. 5 is a schematic explanatory view illustrating a state in which the artificial knee joint 1 of the embodiment is mounted on to a knee.
Figure 5B:
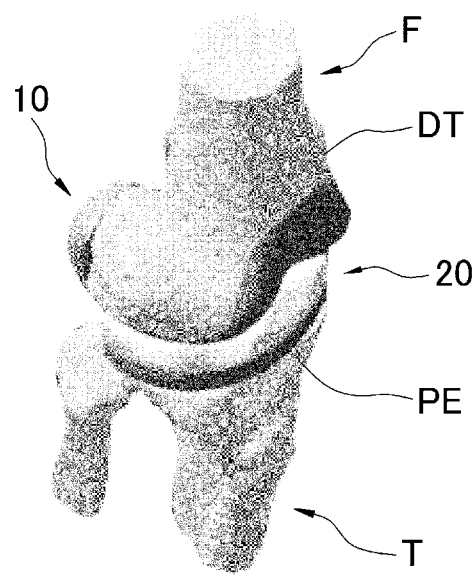
Figure 6A:
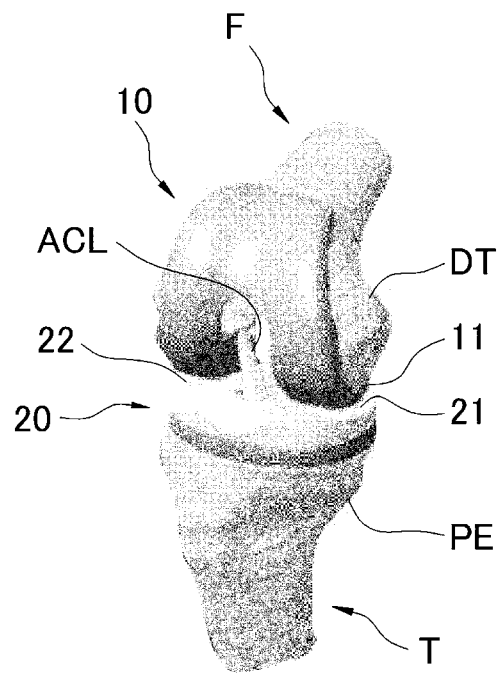
FIG. 6 is a schematic diagram illustrating the state in which the artificial knee joint 1 of the embodiment is mounted on to a knee and a state the knee is slightly bent.
Figure 6B:
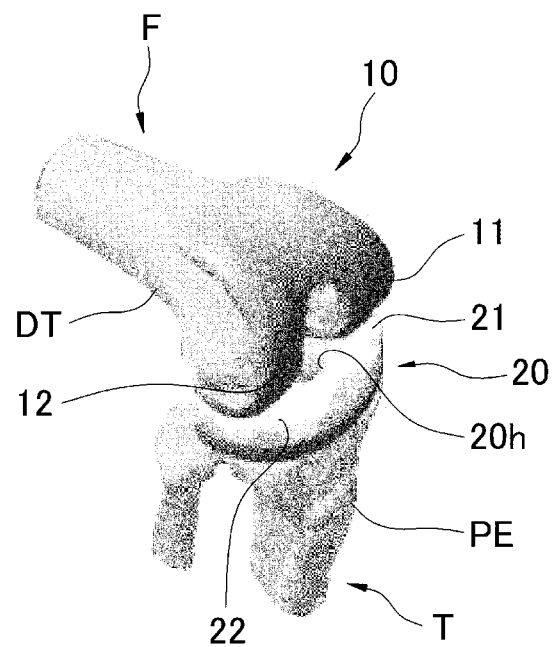
Figure 7A:
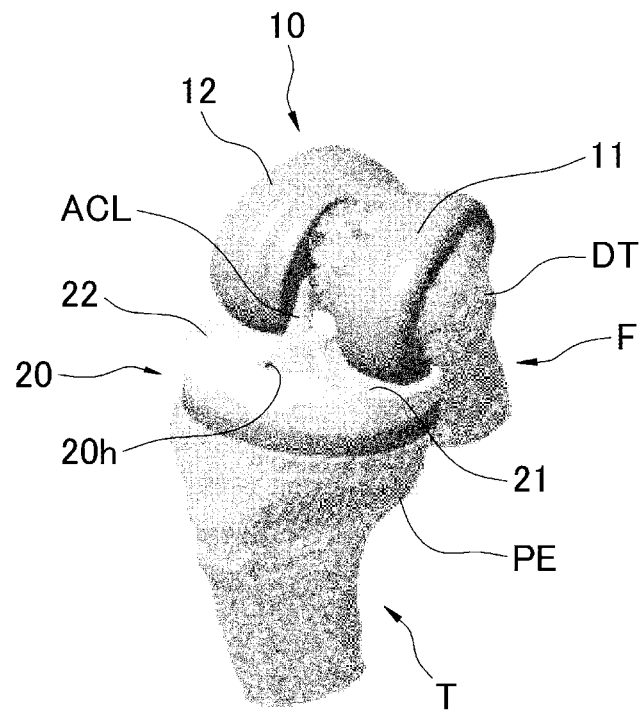
FIG. 7 is a schematic diagram illustrating the artificial knee joint 1 of the embodiment while the knee is deeply bent.
Figure 7B:
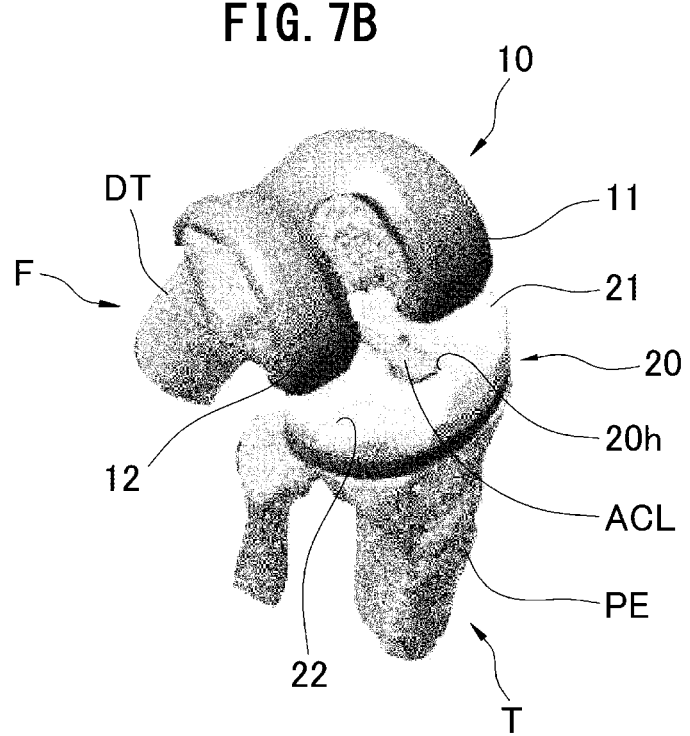
Figure 8:
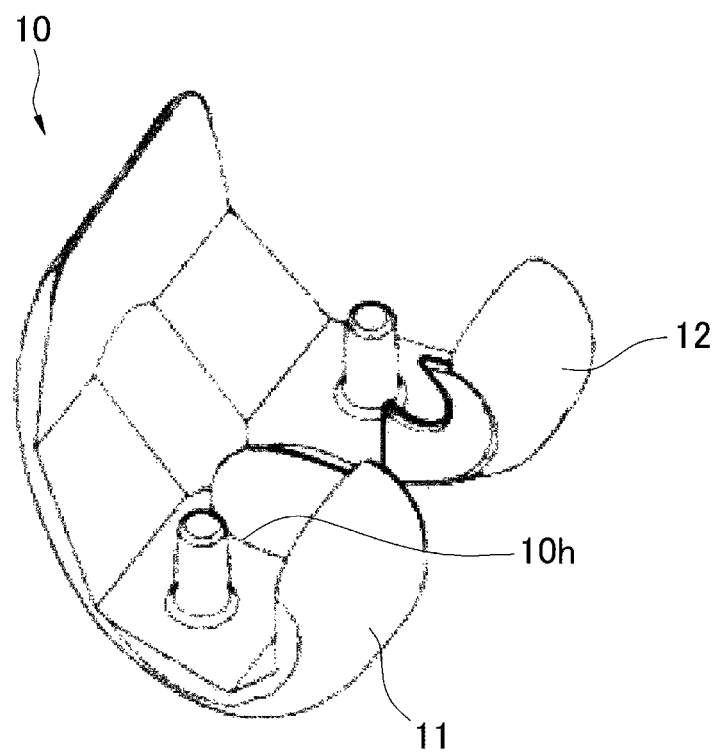
FIG. 8 is a perspective view schematically illustrating a femur member 10 of the artificial knee joint 1 of the embodiment.
Figure 9A:
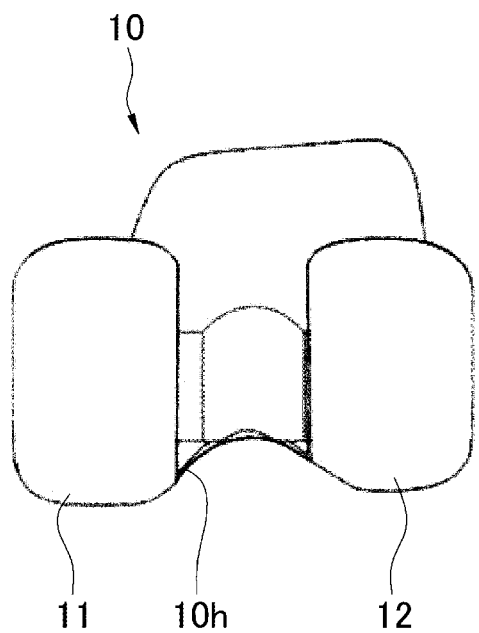
FIGS. 9(A) and 9(B) are rear and front views schematically illustrating the femur member 10 of the artificial knee joint 1 of the embodiment, respectively.
Figure 9B:
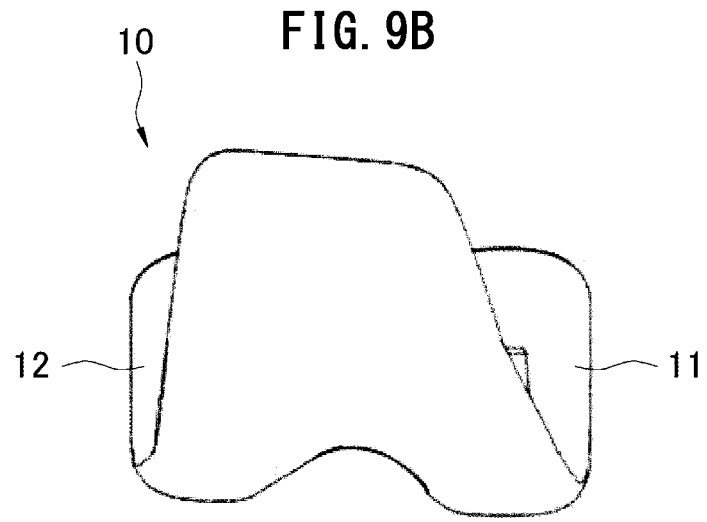

As illustrated in FIGS. 5 to 7, the femur member 10 is mounted on a distal end DT of the femur F. The femur member 10 includes a part (hereinafter, simply referred to as a medial condyle 11) mounted on a medial condyle MC of the femur F and a part (hereinafter, simply referred to as a lateral condyle 12) mounted on a lateral condyle LC of the femur F. Specifically, each of the medial condyle 11 and the lateral condyle 12 is formed into a substantial J-shape, namely, an arc shape in side view. In the femur member 10, a gap 10h is formed between the medial condyle 11 and the lateral condyle 12. That is, in the femur member 10, surfaces of the medial condyle 11 and lateral condyle 12 are formed into the substantially same shape as the distal end DT of the normal femur F of a human body, the surfaces coming into contact with the tibia member 20 (see FIGS. 8 and 9).

(Tibia Member 20)

As illustrated in FIGS. 5 to 7, the tibia member 20 is mounted on a proximal end PE of the tibia T. The tibia member 20 includes a portion corresponding to the medial condyle MC of the tibia T (hereinafter, simply referred to as a medial condyle 21) and a portion corresponding to the lateral condyle LC of the femur F (hereinafter, simply referred to as a lateral condyle 22) in an upper portion of the tibia member 20 (see FIGS. 10 to 13).

In the tibia member 20, a notch 20s is formed between the medial condyle 21 and lateral condyle 22, which are located in a rear portion of the tibia member 20. Specifically, the notch 20s is formed such that the posterior cruciate ligament PCL can be disposed at a position at which the original posterior cruciate ligament PCL exists (see FIGS. 10, 11, 14, and 15).

Figure 16A:
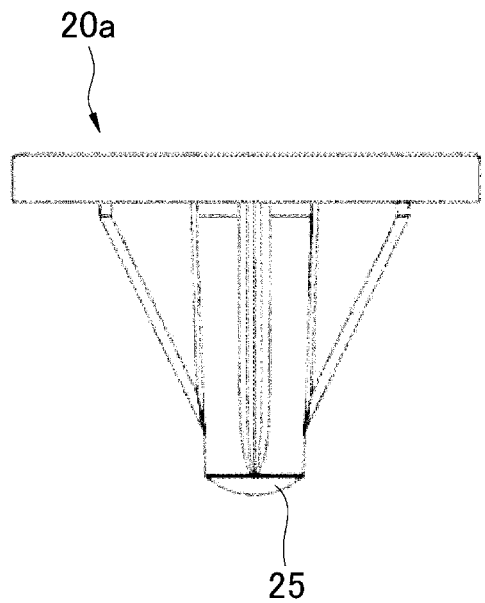
FIGS. 16(A) and 16(B) are right and left side views schematically illustrating the base part 20a in the tibia member 20 of the artificial knee joint 1 of the embodiment, respectively.
Figure 16B:
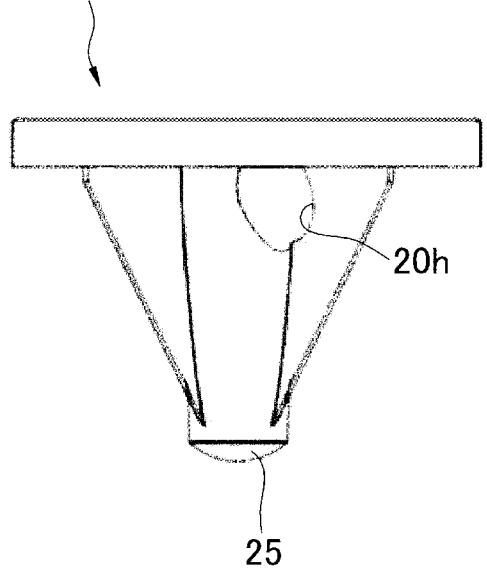

Additionally, in the tibia member 20, a ligament insertion hole 20h piercing the tibia member 20 is provided between the medial condyle 21 and lateral condyle 22, which are located in a front portion of the tibia member 20. Specifically, the ligament insertion hole 20h is formed such that the anterior cruciate ligament ACL can be disposed at the position at which the original anterior cruciate ligament ACL exists when the tibia member 20 is mounted on the tibia T. More particularly, the ligament insertion hole 20h is provided so as to pierce the tibia member 20 diagonally downward (inward) from the top surface of the tibia member 20 (see FIGS. 14 and 16).

In the tibia member 20, an intercondylar eminence 23 is formed between the medial condyle 21 and the lateral condyle 22 and between the ligament insertion hole 20h and the notch 20s (see FIGS. 10 to 13).

That is, the upper portion of the tibia member 20 is formed into the shape similar to the proximal end PE of the normal tibia T of the human body.

(Mounting Example of Artificial Knee Joint 1 of the Embodiment)

The artificial knee joint 1 of the embodiment having the above configuration is mounted as follows.

As to the knee on which the artificial knee joint 1 is mounted, the distal end DT of the femur F is partially cut off, and formed into the shape on which the femur member 10 can be mounted. Specifically, the medial condyle MC and lateral condyle LC of the femur F are formed into the shape that comes into close contact with inner surfaces of the medial condyle 11 and lateral condyle 12 of the femur member 10.

The proximal end PE of the tibia T is also partially cut off, and is formed into the shape on which the tibia member 20 can be mounted. Specifically, the proximal end PE of the tibia T is cut off such that an end surface of the proximal end PE of the tibia T becomes flat. Because the tibia member 20 also includes a stem 25, a hole into which the stem 25 is inserted is also provided in the end surface of the proximal end PE of the tibia T.

At this point, the anterior cruciate ligament ACL and the posterior cruciate ligament PCL are cut off in the ligaments connecting the distal end DT of the femur F and the proximal end PE of the tibia T.

In the case that the posterior cruciate ligament PCL is preserved, only the anterior cruciate ligament ACL is cut off.

Then, the femur member 10 is mounted so as to cover the distal end DT of the femur F. Therefore, at the distal end DT of the femur F, the medial condyle MC and lateral condyle LC of the femur Fare covered with the medial condyle 11 and lateral condyle 12 of the femur member 10 (see FIGS. 5 to 7).

The tibia member 20 is mounted on the proximal end PE of the tibia T. At this point, the stem 25 is inserted into the hole provided in the end surface of the proximal end PE of the tibia T, and the tibia member 20 is mounted on the proximal end PE of the tibia T such that a bottom surface 20a of the tibia member 20 comes into surfaces contact with the end surface of the proximal end PE of the tibia T. Therefore, at the proximal end PE of the tibia T, the medial condyle MC and lateral condyle LC of the tibia T are replaced for the medial condyle 21 and lateral condyle 22 of the tibia member 20. An intercondylar eminence E of the tibia T is replaced for the intercondylar eminence 23 of the tibia member 20 (see FIGS. 5 to 7).

(Reconstruction of Posterior Cruciate Ligament PCL)

The femur member 10 includes the gap 10h between the medial condyle 11 and the lateral condyle 12, and the notch 20s is formed between the medial condyle 21 and lateral condyle 22 in the rear portion of the tibia member 20. Therefore, a space communicating the proximal end PE of the tibia T and the distal end DT of the femur F with each other through the notch 20s and the gap 10h is formed. That is, the space is formed in the portion at which the posterior cruciate ligament PCL exists even if the femur member 10 and the tibia member 20 are mounted on the proximal end PE of the tibia T and the distal end DT of the femur F.

When the reconstruction ligament is disposed so as to pass through the notch 20s and the gap 10h, the posterior cruciate ligament PCL can be reconstructed. Specifically, at the distal end DT of the femur F, one of ends of the reconstruction ligament is joined to the position to which once one of ends of the original posterior cruciate ligament PCL is connected. On the other hand, at the proximal end PE of the tibia T, the other end of the reconstruction ligament is joined to the position to which once the other end of the original posterior cruciate ligament PCL is connected. Therefore, the reconstruction ligament is disposed at the position where once the original posterior cruciate ligament PCL exists, so that the posterior cruciate ligament PCL can be reconstructed by the reconstruction ligament.

In the case that the posterior cruciate ligament PCL is preserved, the posterior cruciate ligament PCL can be disposed in the notch 20s and the gap 10h. That is, the posterior cruciate ligament PCL can be disposed at the original position.

(Reconstruction of Anterior Cruciate Ligament ACL)

In the artificial knee joint 1 of the embodiment, the tibia member 20 includes the ligament insertion hole 20h piercing the tibia member 20. As described above, the ligament insertion hole 20h is provided such that the anterior cruciate ligament ACL can be disposed at the position at which once the original anterior cruciate ligament ACL exists when the tibia member 20 is mounted on the tibia T.

Additionally, the femur member 10 includes the gap 10h between the medial condyle 11 and the lateral condyle 12. Therefore, the space is formed in the portion at which the anterior cruciate ligament ACL exists even if the femur member 10 and the tibia member 20 are mounted on the distal end DT of the femur F.

When the reconstruction ligament ACL is disposed so as to pass through the ligament insertion hole 20h and the gap 10h, the anterior cruciate ligament ACL can be reconstructed.

Specifically, at the distal end DT of the femur F, one of ends of the reconstruction ligament ACL is joined to the position to which one of ends of the original anterior cruciate ligament ACL is connected. The other end of the reconstruction ligament ACL is inserted into the ligament insertion hole 20h, and joined to the proximal end PE of the tibia T.

The hole connected to the ligament insertion hole 20h is provided in the proximal end PE of the tibia T, and the other end of the reconstruction ligament ACL is inserted into the hole so as to be fixed to the proximal end PE of the tibia T.

At this point, the ligament insertion hole 20h is provided such that the anterior cruciate ligament ACL can be disposed at the position at which once the original anterior cruciate ligament ACL exists. Specifically, the ligament insertion hole 20h is formed such that the position of the opening of the ligament insertion hole 20h on the top surface of the tibia member 20 is in the position to which once the other end of the original anterior cruciate ligament ACL is connected at the proximal end PE of the tibia T. When the reconstruction anterior cruciate ligament ACL is inserted into the ligament insertion hole 20h, the other end of the reconstruction ligament ACL is disposed at the position to which once the other end of the original anterior cruciate ligament ACL is connected at the proximal end PE of the tibia T.

Accordingly, when the other end of the reconstruction anterior cruciate ligament ACL is disposed at the proximal end PE of the tibia T through the ligament insertion hole 20h, the reconstruction ligament ACL can be disposed at the position (or the neighborhood of the position) where once the original anterior cruciate ligament ACL exists, so that the anterior cruciate ligament ACL can be reconstructed by the reconstruction ligament ACL.

Thus, in the artificial knee joint 1 of the embodiment, not only the posterior cruciate ligament PCL but also the anterior cruciate ligament ACL can be reconstructed. That is, because the ligament insertion hole 20h is provided in the tibia member 20, when the reconstruction ligament ACL is inserted into the ligament insertion hole 20h, the reconstruction ligament ACL can be provided so as to join the distal end DT of the femur F and the proximal end PE of the tibia T to each other. Additionally, the mounted reconstruction ligament ACL can be disposed at the position where once the anterior cruciate ligament ACL exists in the knee replaced for the artificial knee joint 1. Accordingly, in the artificial knee joint 1 of the embodiment, in addition to the posterior cruciate ligament PCL, the anterior cruciate ligament ACL can be reconstructed so as to be in the substantially same state as the knee replaced for the artificial knee joint 1.

As described above, the ligament insertion hole 20h is provided at the position where once the anterior cruciate ligament ACL exists in the knee replaced for the artificial knee joint 1. However, there is no limitation to a method for deciding the position or an angle (an angle relative to an axis direction of the tibia T) of the ligament insertion hole 20h. For example, the position of the anterior cruciate ligament ACL of a person on which the artificial knee joint 1 is mounted is previously checked, and the position where the ligament insertion hole 20h is provided may be decided based on the check.

The positions and angles of the anterior cruciate ligaments ACL of plural persons are measured, and the position where the ligament insertion hole 20h is formed may statistically be decided. Specifically, the tibia member 20 including the ligament insertion hole 20h having a diameter of 5 mm to 12 mm is used. In the top surface of the tibia member 20, the ligament insertion hole 20h is provided such that the center of the opening is disposed at the position of 25% to 50% from the front end of the tibia member 20, and such that the center of the opening is disposed at the position of 0 to 10% from right to left from the center in the right and left directions. When the other end of the reconstruction ligament ACL is disposed in the ligament insertion hole 20h of the tibia member 20, the reconstruction ligament ACL can be disposed at the position of the anterior cruciate ligament ACL of a person on which the artificial knee joint 1 is mounted. Specifically, when the reconstruction ligament ACL is regarded as one string, and when a center axis of the string is disposed so as to pass through the center (the center in the surface (the top surface of the tibia member 20) on the side of femur member 10) of the opening, the reconstruction ligament ACL can be disposed at the position of the anterior cruciate ligament ACL of a person on which the artificial knee joint 1 is mounted. Therefore, the anterior cruciate ligament ACL can move similarly to the anterior cruciate ligament of a human (see a practical example).

Study results of the inventors show that, in bending and stretching the knee, an anterior cruciate ligament ACL of a person changes depending on the bending angle between the state in which the anterior cruciate ligament ACL is stretched by applying the tensile force and the state in which the tensile force is weakened to slightly relieve the anterior cruciate ligament ACL. It is also found that the change slightly depends on a distance from the center axis of the anterior cruciate ligament ACL or the position. However, when the reconstructed anterior cruciate ligament ACL is disposed in the ligament insertion hole 20h formed at the above position, the reconstructed anterior cruciate ligament ACL can reproduce various tension states according to the distance from the center axis of the anterior cruciate ligament ACL or the position. Additionally, the function of the anterior cruciate ligament ACL can be equalized to the anterior cruciate ligament of the human.

In addition to the disposition of the reconstructed anterior cruciate ligament ACL, when the artificial knee joint 1 includes the shapes of the medial condyle 21 and lateral condyle 22 of the tibia member 20 and the intercondylar eminence 23, the movement of the anterior cruciate ligament ACL can be brought closer to the movement of the original anterior cruciate ligament ACL of the person on which the artificial knee joint 1 is mounted.

The position of the opening of the ligament insertion hole 20h in the tibia member 20 depends slightly on sexuality or a race even within the above range, each patient may change the position according to a corresponding category. For example, the tibia member 20 in which the ligament insertion hole 20h having a diameter of 6 mm to 9 mm is formed such that the center of the opening is disposed at the position of 33% to 46% in the top surface of the tibia member 20, and such that the center of the opening is disposed at the position of 0 to 5% from right to left from the center in the right and left directions in the top surface of the tibia member 20. When the other end of the reconstruction ligament ACL is disposed in the ligament insertion hole 20h of the tibia member 20, the reconstruction ligament ACL can be disposed at the position of the anterior cruciate ligament ACL of a person on which the artificial knee joint 1 is mounted.
(The Case that Plural Ligament Insertion Holes 20h are Provided)

Figure 37:
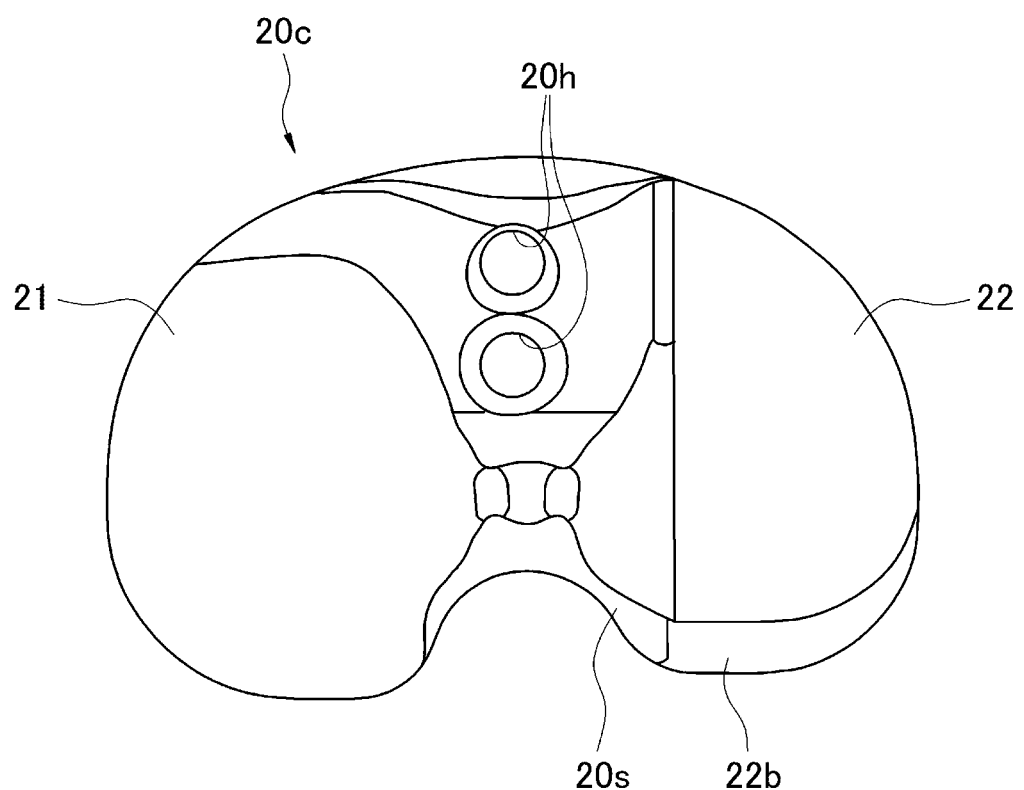
FIG. 37 is a plan view schematically illustrating a contact part 20c in which two ligament insertion holes 20h are provided.
Figure 38:
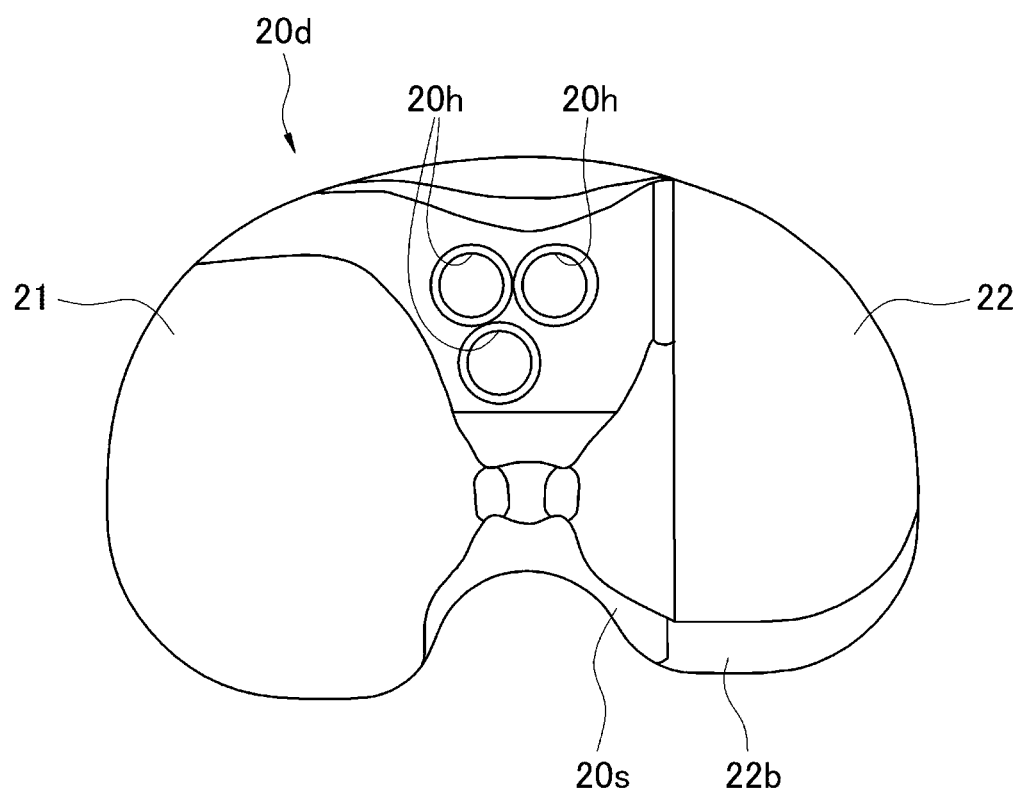
FIG. 38 is a plan view schematically illustrating a contact part 20d in which three ligament insertion holes 20h are provided.

As described above, the study results of the inventors show that, in the anterior cruciate ligament ACL, the tensile force generating status depends on the distance from the center axis when the knee is bent and stretched. In the normal anterior cruciate ligament ACL, it is found that the anterior cruciate ligament ACL is formed by plural bundles of ligaments, and that the tensile force generating status depends on each bundle when the knee is bent and stretched. Accordingly, in the case that the anterior cruciate ligament ACL to be reconstructed is formed by the plural bundles of reconstruction ligaments, the reconstructed anterior cruciate ligament can be brought closer to the function of the original anterior cruciate ligament ACL using the artificial knee joint 1 of the embodiment. In this case, the reconstruction anterior cruciate ligament ACL formed by the plural bundle of reconstruction ligaments may wholly inserted into one ligament insertion hole 20h formed in the tibia member 20, or plural ligament insertion holes 20h may be provided in the tibia member 20 to insert one bundle (or plural bundles) into each ligament insertion hole 20h. In this case, the tensile force generated in each bundle is brought closer to the tensile force generated in the bundle of the ligaments disposed at the same position in the anterior cruciate ligament ACL to be reconstructed, so that the function closer to the original anterior cruciate ligament ACL can be exerted. In this case, the positions where the plural ligament insertion holes 20h are provided such that all the ligament insertion holes 20h (or almost all the ligament insertion holes 20h) are disposed in the above range where the ligament insertion hole 20h is formed (that is, the top surface of the tibia member 20, the position of 25% to 50% from the front end and the position of 0 to 10% from right to left from the center in the right and left directions). For example, in the case that the reconstruction anterior cruciate ligament ACL formed by the two bundles of reconstruction ligaments is provided, two ligament insertion holes 20h are provided at the positions as illustrated in FIG. 37. Because the whole (or the center) of the ligament insertion hole 20h is disposed in the above range, the whole (or the center) of the bundles of the reconstruction ligaments are also disposed in the above range. Therefore, the tensile force generated in the bundle of reconstruction ligaments disposed in each ligament insertion hole 20h can be brought closer to the tensile force generated in the bundle of the ligaments disposed at the same position in the anterior cruciate ligament ACL to be reconstructed. In the case that the reconstruction anterior cruciate ligament ACL formed by the three bundles of reconstruction ligaments is provided, three ligament insertion holes 20h are provided at the positions as illustrated in FIG. 38. The whole (or the center) of the ligament insertion holes 20h can be disposed in the above range. When the excessively large ligament insertion hole 20h is provided, possibly the excessively large ligament insertion hole 20h communicates and interferes with the adjacent ligament insertion hole 20h. When the excessively small ligament insertion hole 20h is provided, possibly the excessively small ligament insertion hole 20h interferes with the bundle of ligaments to break the bundle of ligaments. Accordingly, in the case that the plural ligament insertion holes 20h are provided, preferably a size (diameter) of each ligament insertion hole 20h ranges from about 1 mm to about 6 mm although it depends on the number of holes to be provided. For example, in the case that the two ligament insertion holes 20h are provided at the positions as illustrated in FIG. 37, preferably the diameter of the ligament insertion hole 20h ranges from about 4 mm to about 6 mm. Similarly, in the case that the three ligament insertion holes 20h are provided at the positions as illustrated in FIG. 38, preferably the diameter of the ligament insertion hole 20h ranges from about 3 mm to about 6 mm.

(Intercondylar Eminence 23)

In the tibia member 20, the intercondylar eminence 23 is formed between the medial condyle 21 and the lateral condyle 22 and between the ligament insertion hole 20h and the notch 20s. Preferably the height and shape of the intercondylar eminence 23 are formed substantially equal to those of the intercondylar eminence 23 in the knee replaced for the artificial knee joint 1. Force attracting the lateral condyle 12 of the femur member 10 onto the side of the medial condyle 21 of the tibia member 20 is generated when the anterior cruciate ligament ACL is reconstructed. When the lateral condyle 22 is formed into the flat surface, the lateral condyle 12 of the femur member 10 moves easily toward the inside. However, when the height of the intercondylar eminence 23 is formed as described above, the movement of the lateral condyle 12 of the femur member 10 is limited, so that the knee replaced for the artificial knee joint 1 can be stabilized.

In a healthy knee, the intercondylar eminence 23 generates interaction by contacting with the anterior cruciate ligament ACL or the posterior cruciate ligament PCL, and the interaction properly generates the tensile force in the anterior cruciate ligament ACL or the posterior cruciate ligament PCL. Accordingly, when the reconstructed anterior cruciate ligament ACL is disposed at a proper position (that is, the ligament insertion hole 20h of the tibia member 20 is formed at a proper position) to form the intercondylar eminence 23, the movement of the anterior cruciate ligament ACL or the generated tensile force can be equalized to that of an anterior cruciate ligament of a human.

As used herein, the height of the intercondylar eminence 23 means a height from the top surface of the lateral condyle 22 of the tibia member 20. However, the height is not necessarily equalized to that of the intercondylar eminence 23 in the knee replaced for the artificial knee joint 1. For example, the height may be set to about 70% to about 120% of height of the intercondylar eminence 23 in the knee replaced for the artificial knee joint 1.

A slight recess 24 similar to the organism tibia T is provided at a leading end of the intercondylar eminence 23. In the anterior cruciate ligament ACT which interferes with the intercondylar eminence 23, the tensile force can properly be generated by providing the recess 24. In particular, in the case that the anterior cruciate ligament ACL is formed by the plural bundles of reconstruction ligaments, the provision of the slight recess 24 changes the interference state in each bundle of reconstruction ligaments when the plural bundles of reconstruction ligaments interfere with the leading end of the intercondylar eminence 23. That is, the tensile force generated in each bundle of reconstruction ligaments is adjusted so as to be in a proper state, so that the movement of the anterior cruciate ligament ACL or the generated tensile force can be equalized to that of an anterior cruciate ligament of a human.

(Medial Condyle 21 and Lateral Condyle 22 of Tibia Member 20)

Although there is no limitation to the shapes of the medial condyle 21 and lateral condyle 22 of the tibia member 20, desirably the shapes of the medial condyle 21 and lateral condyle 22 is formed into the shape similar to the organism tibia T. Specifically, the medial condyle 21 is larger than the lateral condyle 22 in planar view, and the medial condyle 21 has the concave curve. However, desirably the lateral condyle 22 is formed into a flat surface (see FIGS. 10 to 13).

In this case, even if the posterior cruciate ligament PCL is present while the anterior cruciate ligament ACL is absent, the knee becomes unstable because the lateral condyle 22 is formed into the flat surface. That is, the lateral condyle 12 of the femur member 10 slips back and forth or from side to side with respect to the lateral condyle 22 of the tibia member 20, the knee cannot stably move. On the other hand, in the artificial knee joint 1 of the embodiment, because the anterior cruciate ligament ACL is reconstructed, the lateral condyle 12 of the femur member 10 can be attracted toward the lateral condyle 22 of the tibia member 20 by the reconstructed anterior cruciate ligament ACL. Accordingly, even if the lateral condyle 22 is formed into the flat surface, the lateral condyle 12 of the femur member 10 can be moved while being in contact with the lateral condyle 22 of the tibia member 20. Additionally, force attracting the lateral condyle 12 of the femur member 10 toward the inside, namely, the side of the medial condyle 11 of the femur member 10 is also applied to lateral condyle 12. Therefore, in bending the knee, the movement of the lateral condyle 12 of the femur member 10 can be equalized to the natural movement (arc motion) of the knee.

More desirably the medial condyle 21 of the tibia member 20 tilts backward relative to the lateral condyle 22 while the surfaces of the medial condyle 21 and lateral condyle 22 tilt inward. In this case, when the posterior cruciate ligament PCL is present while the anterior cruciate ligament ACL is absent, the knee moves unstable. On the other hand, in the artificial knee joint 1 of the embodiment, because the posterior cruciate ligament PCL and the anterior cruciate ligament ACL are reconstructed, the medial condyle 21 and lateral condyle 22 of the tibia member 20 are formed into the above shape, which allows the artificial knee joint 1 to stably perform the movement closer to the natural knee.

For example, desirably the top surface of the medial condyle 21 tilts backward by about 3° to about 7° with respect to the top surface of the lateral condyle 22. When being mounted on the tibia T, desirably the tibia member 20 tilts inward by about 3° to about 7° with respect to the axis direction of the tibia T (that is, about 3° to about 7° with respect to a direction perpendicular to the axis direction of the stem 25). The top surface of the medial condyle 21 used to determine a backward tilt angle means a surface connecting a front end and a rear end of the medial condyle 21 when the medial condyle 21 is viewed from the side surface. The top surface of the medial condyle 21 used to determine an inward tilt angle means a surface connecting a right end and a left end of the medial condyle 21 when the medial condyle 21 is viewed from the rear surface.

In the tibia member 20, desirably the peripheral portion of the medial condyle 21 and/or lateral condyle 22 is formed into a curved shape. That is, desirably the surface of the medial condyle 21 is continuously connected to the peripheral portion of the medial condyle 21 by the curved surface. Desirably the surface of the lateral condyle 22 is continuously connected to the peripheral portion of the lateral condyle 22 by the curved surface.

Figure 10A:
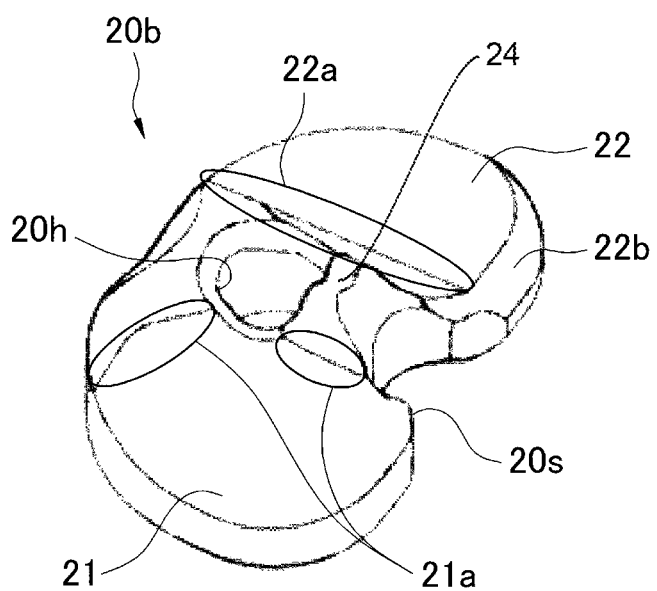
FIG. 10(A) is a perspective view illustrating a contact part 20b in a tibia member 20 of the artificial knee joint 1 of the embodiment.
Figure 10B:
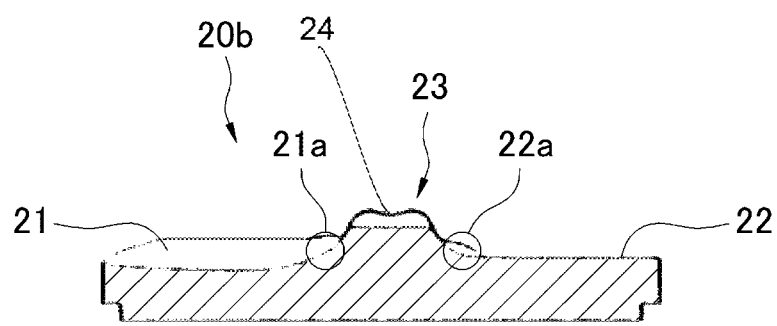
FIG. 10(B) is a sectional view taken along a line XB-XB in FIG. 11.
Figure 11A:
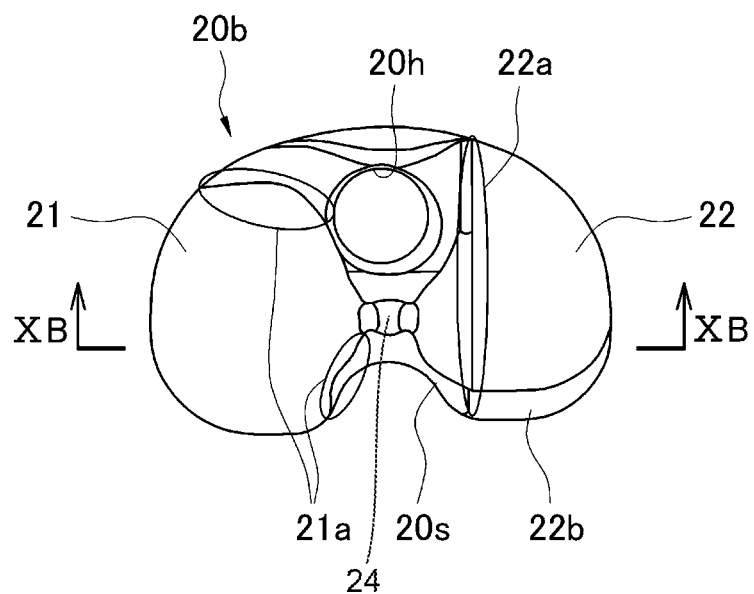
FIGS. 11(A) and 11(B) are plan and bottom views schematically illustrating the contact part 20b in the tibia member 20 of the artificial knee joint 1 of the embodiment, respectively.
Figure 11B:
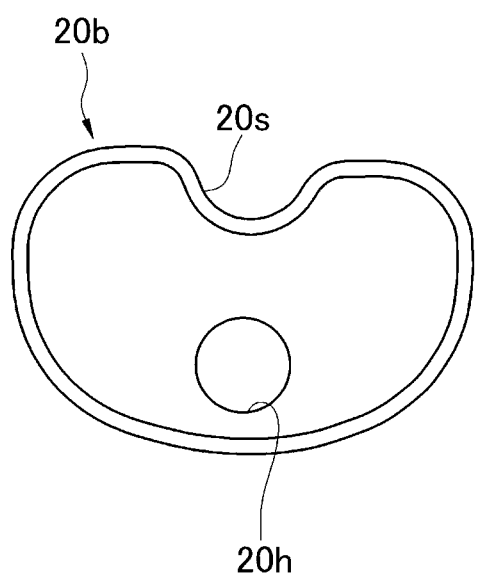
Figure 12A:
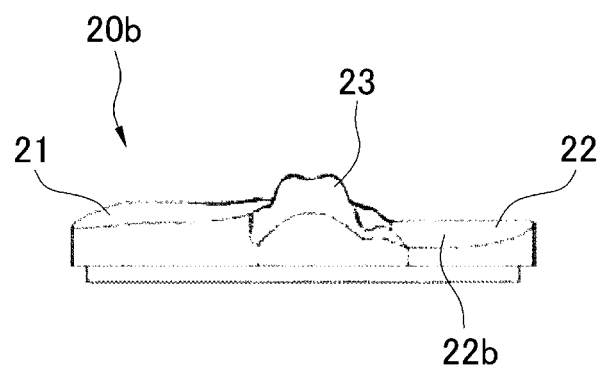
FIGS. 12(A) and 12(B) are rear and front views schematically illustrating the contact part 20b in the tibia member 20 of the artificial knee joint 1 of the embodiment, respectively.
Figure 12B:
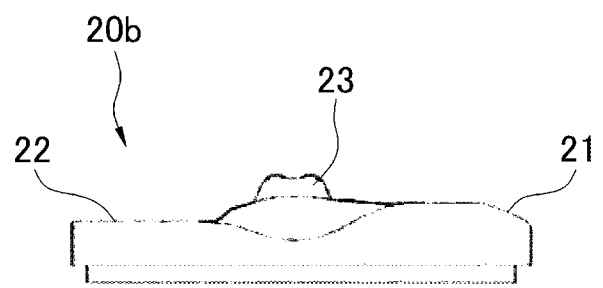

For example, as illustrated in FIGS. 10 and 11, the portion in which the intercondylar eminence 23 and the medial condyle 21 and/or lateral condyle 22 are continuously connected to each other or the portion (in FIGS. 10 and 11, portions 21a and 22a) in which the intercondylar eminence 23 and the medial condyle 21 and/or lateral condyle 22 are continuously connected to other portions is formed into a downward concave curve. That is, in the tibia member 20, desirably the portion except for the portion in which the side surface, rear surface, and front surface of the tibia member 20 are continuously connected to the medial condyle 21 and/or lateral condyle 22 is formed into the downward concave curve.

As illustrated in FIGS. 10 to 14, desirably a boundary portion between the side surface and/or rear surface of the tibia member 20 and the lateral condyle 22 is formed into an outward convex surface. That is, desirably the tibia member 20 is formed so as to become a curved surface (that is, arc section) in which the lateral portion and/or rear portion of the tibia member 20 are smoothly connected to the lateral condyle 22.

When the peripheral portions of the medial condyle 21 and/or lateral condyle 22 are formed as described above, the edge loading can be reduced for the following reason.

The medial condyle 21 of the tibia member 20 is in contact with the surface of the medial condyle 11 of the femur member 10, and the relative position between the medial condyle 21 and the medial condyle 11 changes in bending the knee. At this point, the medial condyle 11 of the femur member 10 moves toward the edge (peripheral portion) of the medial condyle 21 of the tibia member 20 or the intercondylar eminence 23. A portion in which the medial condyle 11 of the femur member 10 and the medial condyle 21 of the tibia member 20 come into strong contact with each other is not generated when the peripheral portion of the medial condyle 21 of the tibia member 20 is formed as described above. Specifically, the state in which a contact area between the medial condyle 11 and the medial condyle 21 is reduced to extremely increase a surface pressure is not generated. That is, because the edge loading can be reduced, the damage of the medial condyle 11 of the femur member 10 and the medial condyle 21 of the tibia member 20 can be prevented to improve durability of the artificial knee joint 1.

Similarly, when the peripheral portion of the lateral condyle 22 of the tibia member 20 is formed as described above, the edge loading can be reduced between the lateral condyle 22 of the tibia member 20 and the lateral condyle 12 of the femur member 10. The damage of the lateral condyle 12 of the femur member 10 and the lateral condyle 22 of the tibia member 20 can be prevented to improve durability of the artificial knee joint 1.

In particular, when the peripheral portion of the lateral condyle 22 of the tibia member 20 is formed as described above, a post-operation movable range can be improved while the edge loading is reduced. Even if the knee joint is replaced for the artificial knee joint 1 of the embodiment, the movable range can be brought close to the healthy knee joint compared with the conventional artificial knee joint when the knee joint is moved (that is, in stretching, bending, or twisting the knee).

In the shape of the curved surface in the boundary portion between the medial condyle 21 and/or lateral condyle 22 and the peripheral portion, there is no particular limitation to a curvature radius as long as the medial condyle 21 and/or the lateral condyle 22 is smoothly connected to the peripheral portion.

The curvature radius of the curved surface in the boundary portion may depend on the position.

The boundary portion between the side surface and/or rear surface and the medial condyle 21 and/or lateral condyle 22 may be formed into not the arc shape but the flat shape. That is, a corner formed between the side surface and/or rear surface and the medial condyle 21 and/or lateral condyle 22 may be chamfered. However, when the boundary portion is formed into the curved surface, the edge loading can be reduced compared with the chamfering, and the post-operation movable range can be improved.

In the embodiment, the side surface and/or rear surface and the lateral condyle 22 of the tibia member 20 are formed into the smoothly-connected curved surface. The boundary portion between the front surface and lateral condyle 22 of the tibia member 20 may also be formed into the smoothly-connected curved surface.

(Tibia Member 20)

The tibia member 20 may integrally be formed from the stem 25 to the medial condyle 21 and the lateral condyle 22. However, desirably the base part 20*a* (FIGS. 14 to 16) fixed to the tibia T of the tibia member 20 and the contact part 20*b* (FIGS. 10 to 13) mounted on the base part 20*a* are separately formed, and the tibia member 20 is formed by a combination of the base part 20*a* and the contact part 20*b*. For example, the medial condyle 21, the lateral condyle 22, the contact part 21*b* including the intercondylar eminence 23 may be formed so as to be detachably attached to the base part 20*a*. In this case, the base part 20*a* in which strength is required can be made of a material having high adaptability and high rigidity (such as titanium and cobalt-chromium organism), and the contact part 20*b* can be made of a material having high sliding and wear-resistant properties (such as ultrahigh molecular polyethylene). Because each region can be made of a material suitable for the required function, the durability can be improved while the smooth movement of the artificial knee joint 1 is ensured.

The ligament insertion hole 20*h* is formed in the base part 20*a* and the contact part 20*b* such that the inner surfaces of the base part 20*a* and the contact part 20*b* are smoothly connected to each other when the base part 20*a* and the contact part 20*b* are assembled. That is, in the state in which the base part 20*a* and the contact part 20*b* are assembled, the opening of the top surface of the base part 20*a* is matched with the opening of the bottom surface of the contact part 20*b*, and the axis directions of the base part 20*a* and the contact part 20*b* are matched with each other. Therefore, the ligament insertion hole 20*h* of the tibia member 20 becomes the through-hole, which is continuously formed from the top surface of the contact part 20*b* to the side surface of the base part 20*a* while the base part 20*a* and the contact part 20*b* are assembled. In the case that the plural ligament insertion holes 20*h* are provided, each ligament insertion hole 20*h* has the above configuration.

Figure 13A:
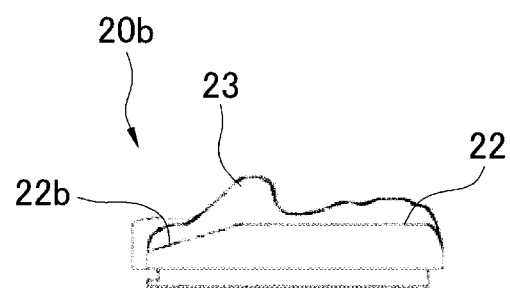
FIGS. 13(A) and 13(B) are right and left side views schematically illustrating the contact part 20b in the tibia member 20 of the artificial knee joint 1 of the embodiment, respectively.
Figure 13B:
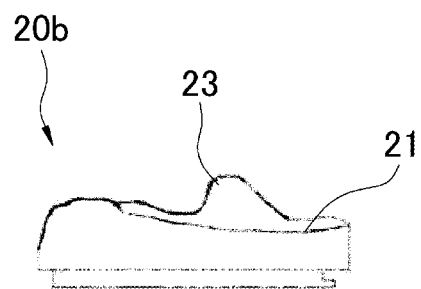
Figure 14A:
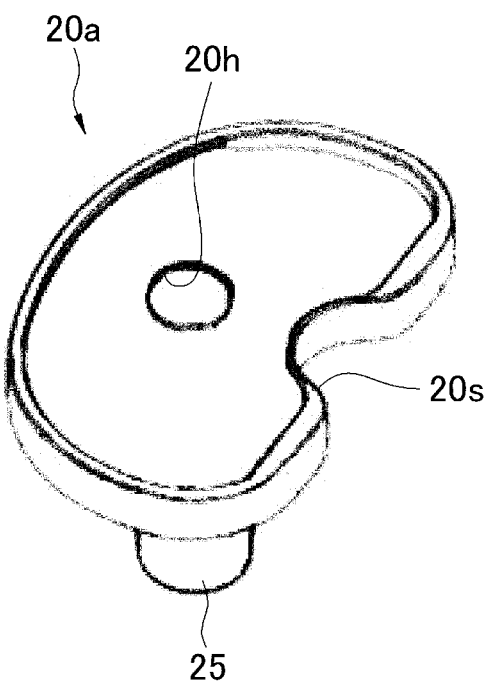
FIGS. 14(A) and 14(B) are perspective and longitudinally sectional views schematically illustrating a base part 20a in the tibia member 20 of the artificial knee joint 1 of the embodiment, respectively.
Figure 14B:
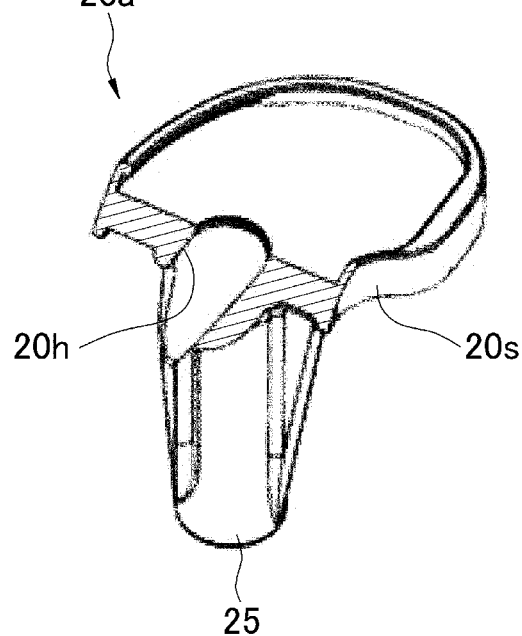
Figure 15A:
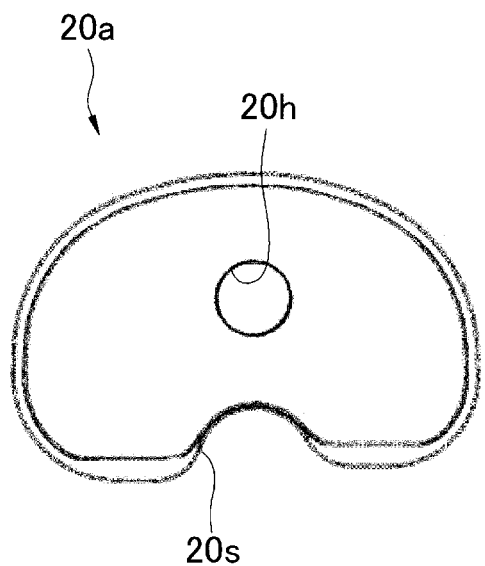
FIGS. 15(A) and 15(B) are plan and bottom views schematically illustrating the base part 20a in the tibia member 20 of the artificial knee joint 1 of the embodiment, respectively.
Figure 15B:
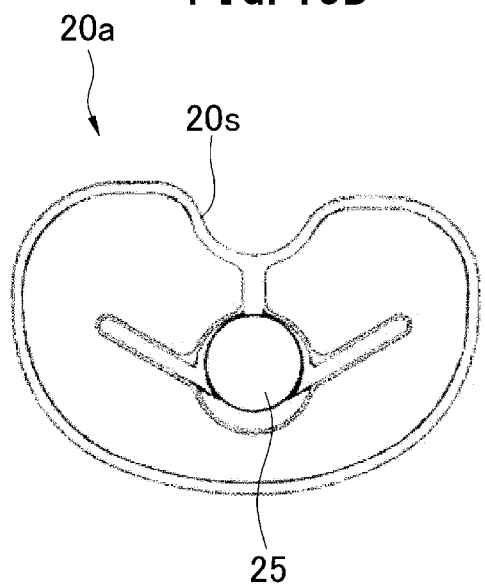

There is no particular limitation to the method for joining the base part 20*a* and the contact part 20*b* to each other. A known method for joining a portion corresponding to the base part 20*a* and a portion corresponding to the contact part 20*b* to each other in the conventional artificial knee joint can be adopted. For example, as illustrated in FIG. 14, a recess is provided in the top surface of the base part 20*a*, and an engagement groove is formed in an inner wall of the recess. On the other hand, as illustrated in FIG. 13, a fitting portion fitted in the recess of the top surface of the base part 20*a* is provided in the lower surface of the contact part 20*b*, and a flange portion that engages with the fitting portion is provided in the side surface of the fitting portion. The fitting portion of the contact part 20*b* is inserted in the recess of the top surface of the base part 20*a* to cause the flange portion to engage with the engagement groove, which allows the base part 20*a* and the contact part 20*b* to be firmly fixed to each other. Even if the femur member 10 and the tibia member 20 move relative to each other, the base part 20*a* and the contact part 20*b* can be prevented from shifting or moving.

Practical Example

The function of the normal anterior cruciate ligament was evaluated, the simulation was performed by an image matching method (see Ishimaru M, Hino K, Miura H etc, J Orthop Res. 2014 May; 32 (5): 619-26. doi: 10.1002/jor.22596.) developed by the inventors in order to verify the layout of the hole necessary for the anterior cruciate ligament to be reconstructed exerts the ligament function of the normal knee when the artificial knee joint of the present invention was used, and a relationship among the load on the organism knee, the knee bending angle, and the ligament length (a distance between one end at which the anterior cruciate ligament is joined to the femur and a one end at which the anterior cruciate ligament is joined to the tibia, hereinafter simply referred to as a ligament length) was obtained.

Figure 17:
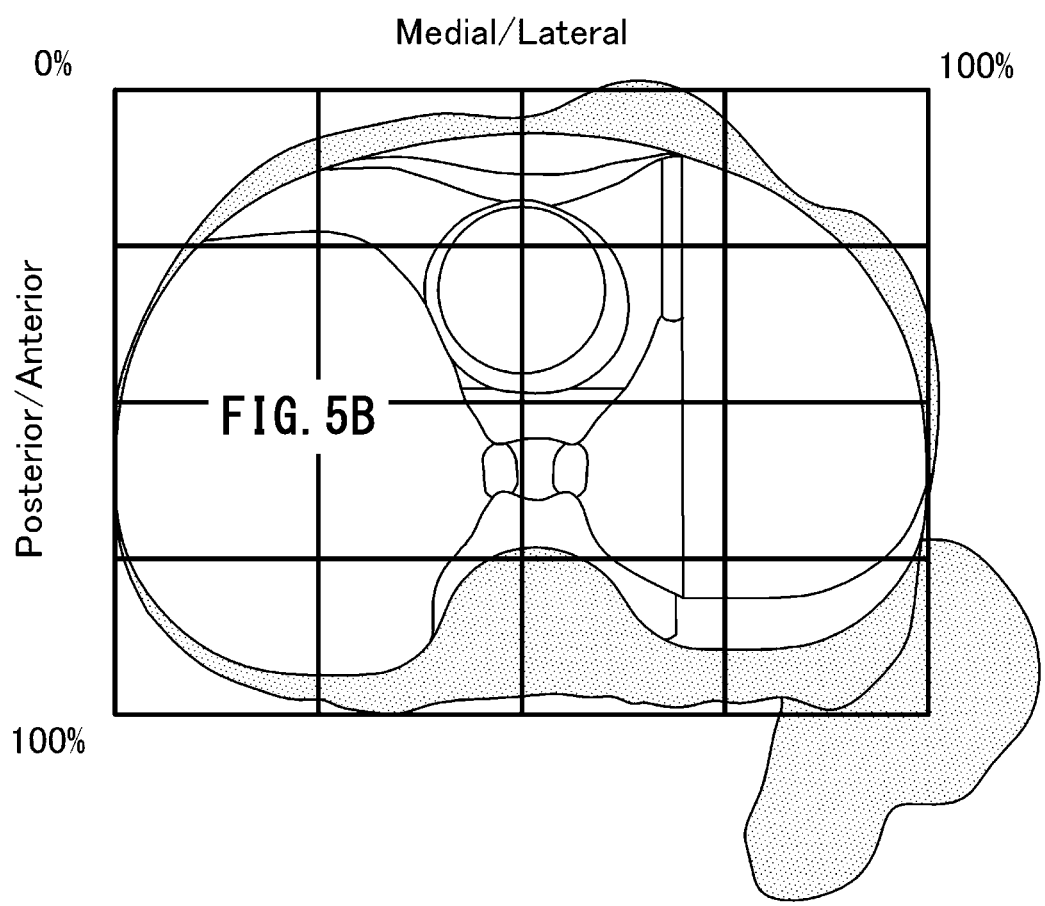
FIG. 17 is a view illustrating a joining position (ligament insertion hole) relationship between an anterior cruciate ligament and a tibia in a simulation of a practical example.
Figure 19:
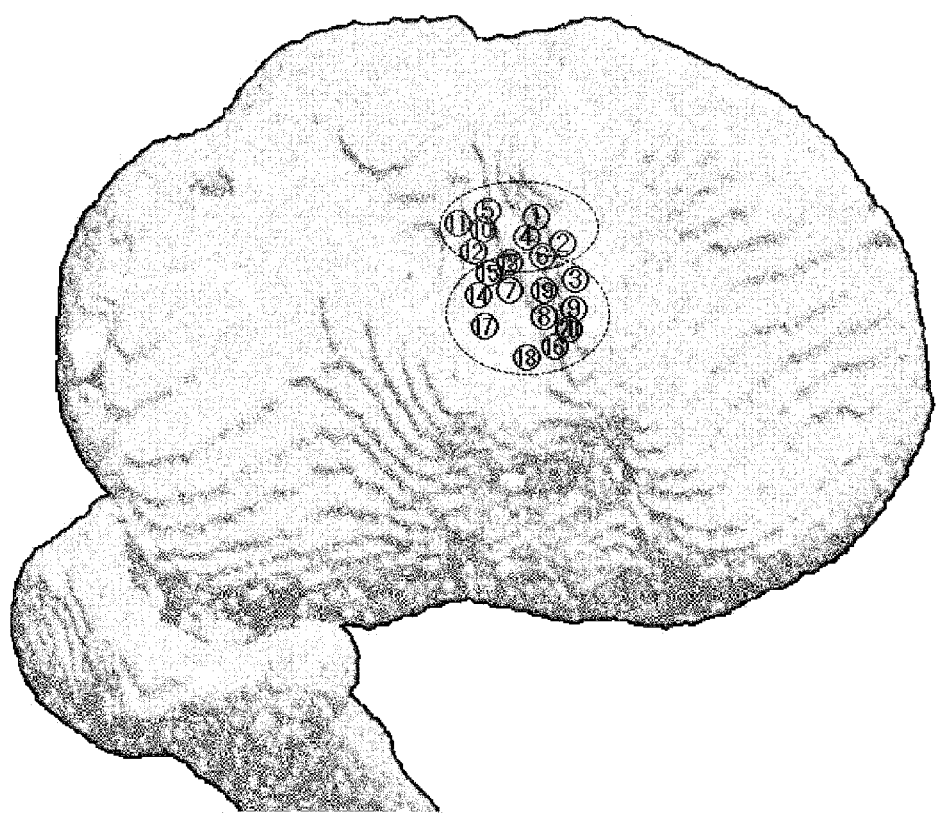
FIG. 19 is a view illustrating the joining position relationship between the anterior cruciate ligament and the femur in the simulation of the practical example.
Figure 20:
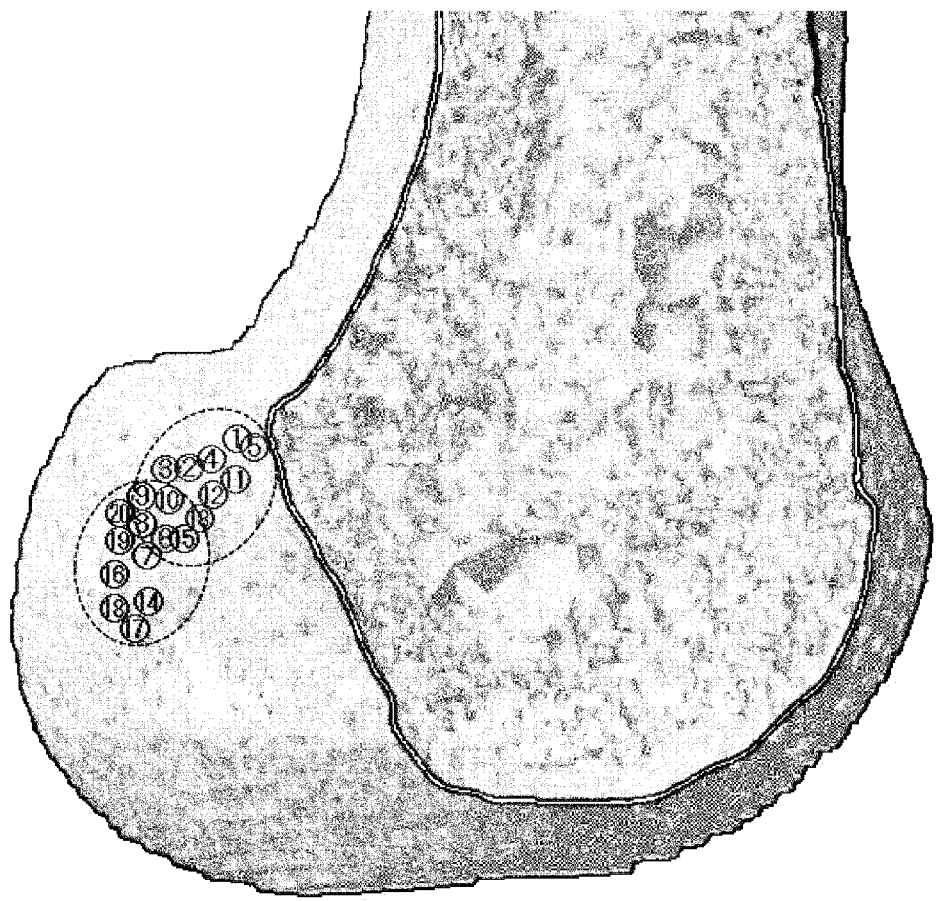
FIG. 20 is a view illustrating the joining position relationship between the anterior cruciate ligament and the femur in the simulation of the practical example.

In a practical example, the relationship between the knee bending angle and each bundle (1 to 20) of anterior cruciate ligaments was simulated with respect to the case that one end of each of the plural bundles (1 to 20) of anterior cruciate ligaments was disposed at the position of the ligament insertion hole (see FIGS. 17 and 19) while the other end of each of the plural bundles (1 to 20) of anterior cruciate ligaments was disposed at the position in FIG. 20. That is, in the simulation, one end of each of the plural bundles (1 to 20) of anterior cruciate ligaments was disposed within the position of 25% to 50% from the front surface and the position of 0 to 10% from right to left from the center in the right and left directions in a front-back direction (Posterior/Anterior) of the tibia member 20 in a coordinate in FIG. 17. In a coordinate in FIG. 18, the other end of each of the plural bundles (1 to 20) of anterior cruciate ligaments was disposed within the position of 12% to 40% from the front surface in a shallow/deep direction of the femur and the position of 10% to 60% in a high/low direction in the front surface direction of the femur.

Figure 18:
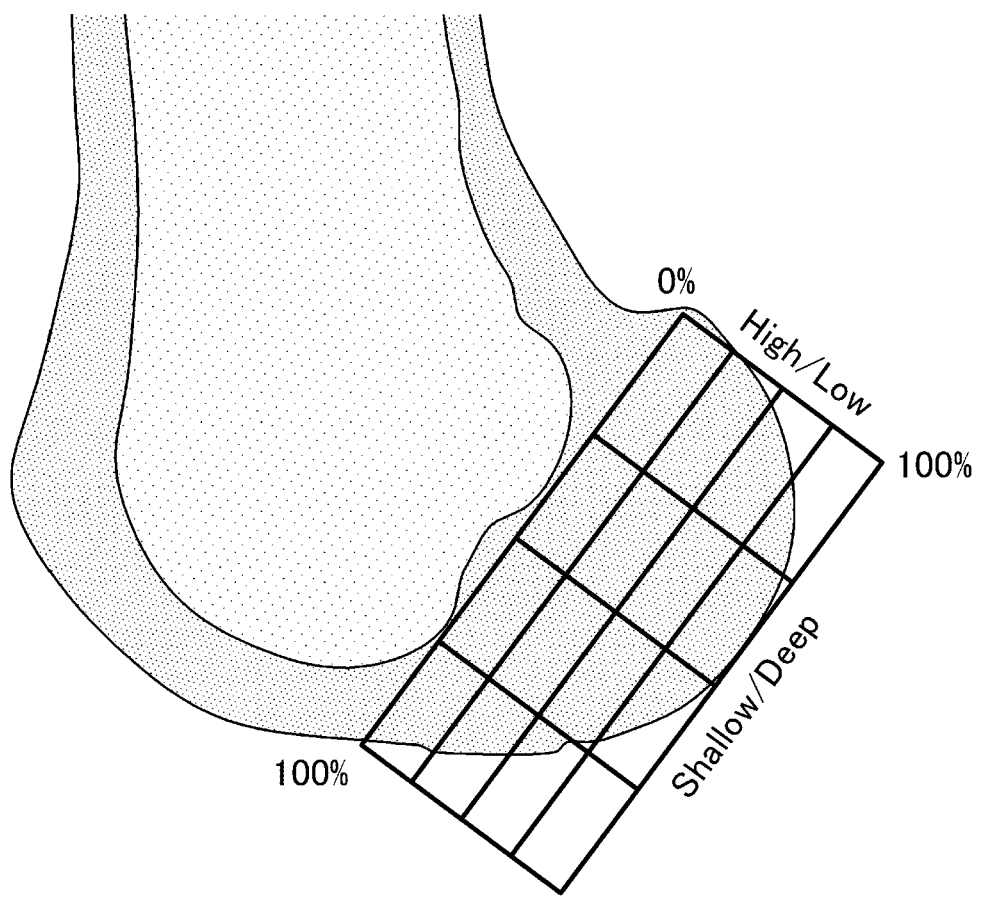
FIG. 18 is a view illustrating the joining position relationship between the anterior cruciate ligament and the tibia in the simulation of the practical example.

In FIGS. 18 and 20, the position of each numerical character indicates the position where the bundles are joined to each other, and the positions having the same numerical character are joined to each other. Numerical characters 1 to 10 indicate a group (AM group) located on the front side of the anterior cruciate ligament, and numerical characters 11 to 20 indicate a group (PL group) located on the rear side of the anterior cruciate ligament.

FIGS. 21 to 31 illustrate results.

Figure 21:
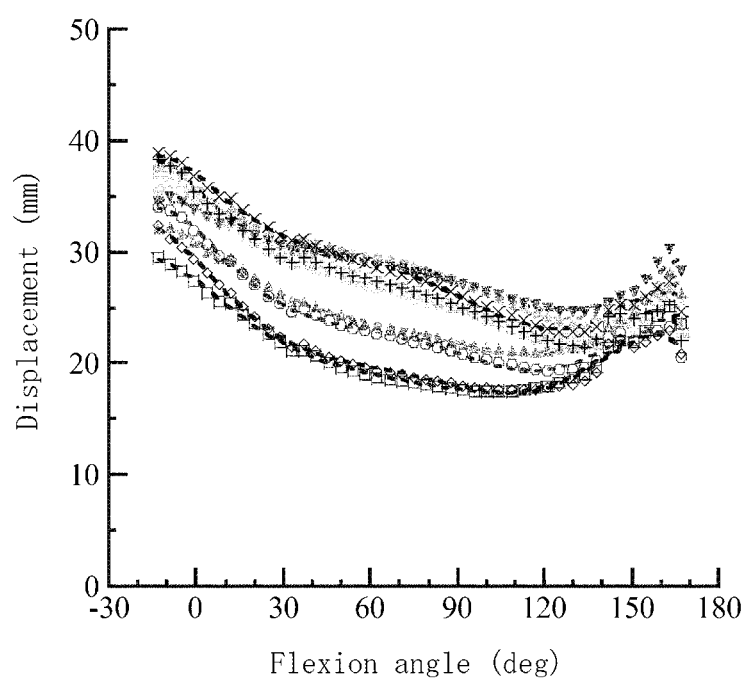
FIG. 21 is a view illustrating a relationship between a bending angle of the knee and a length of the ligament in the practical example.
Figure 22A:
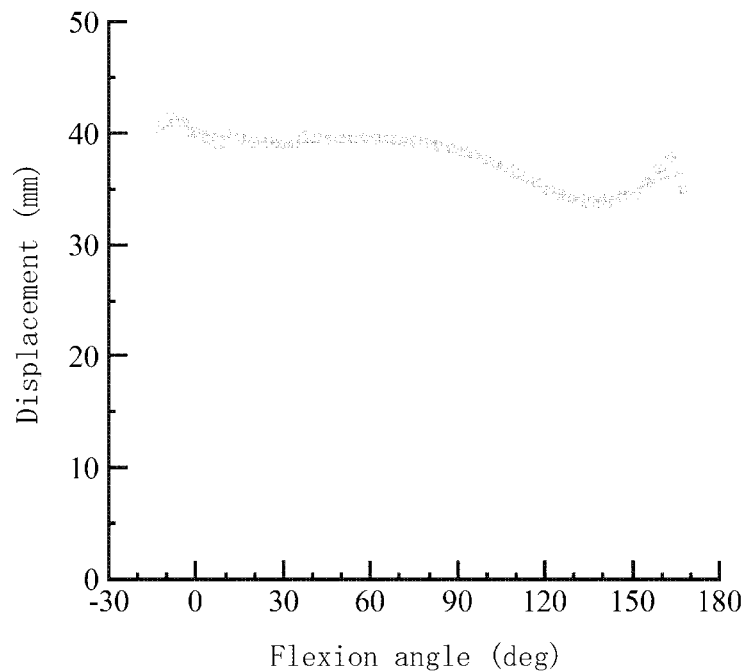
FIG. 22 is a view illustrating a relationship between the bending angle of the knee and the length of the ligament in the practical example.
Figure 22B:
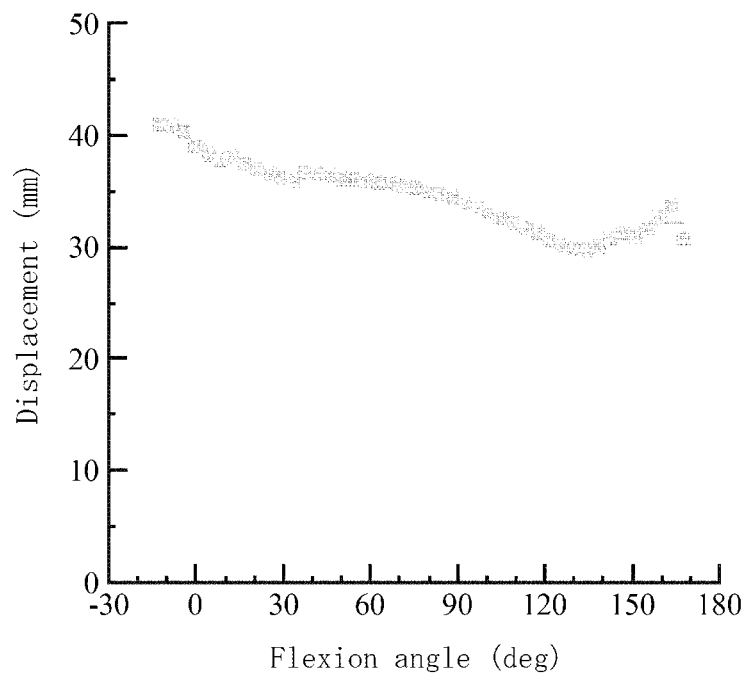
Figure 23A:
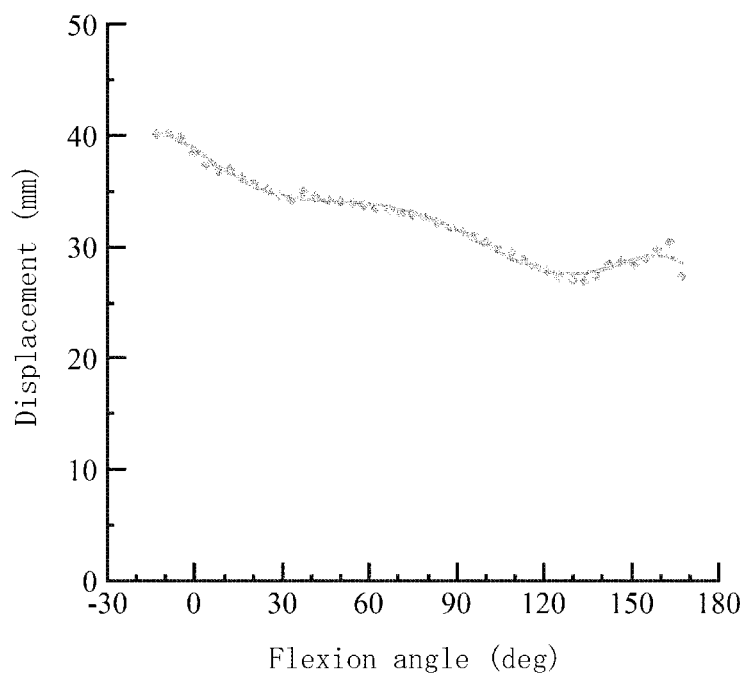
FIG. 23 is a view illustrating a relationship between the bending angle of the knee and the length of the ligament in the practical example.
Figure 23B:
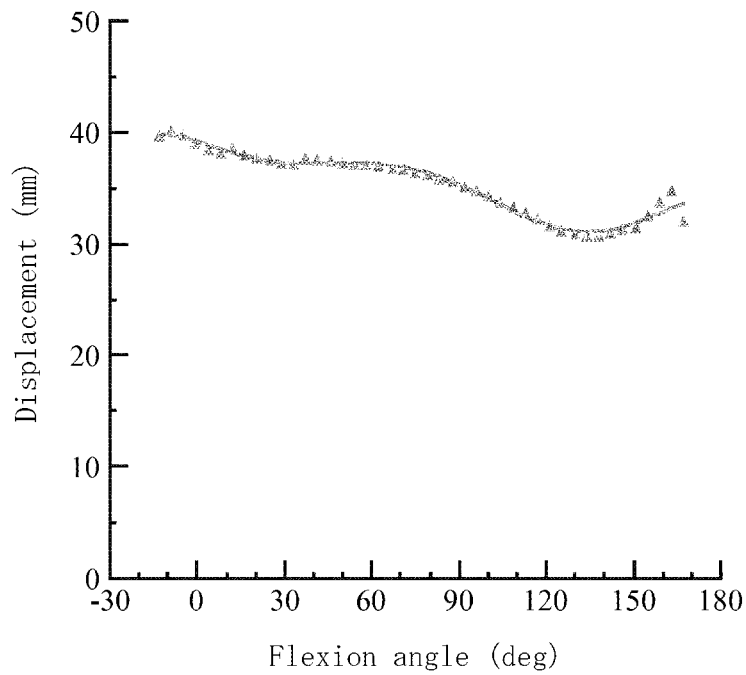
Figure 24A:
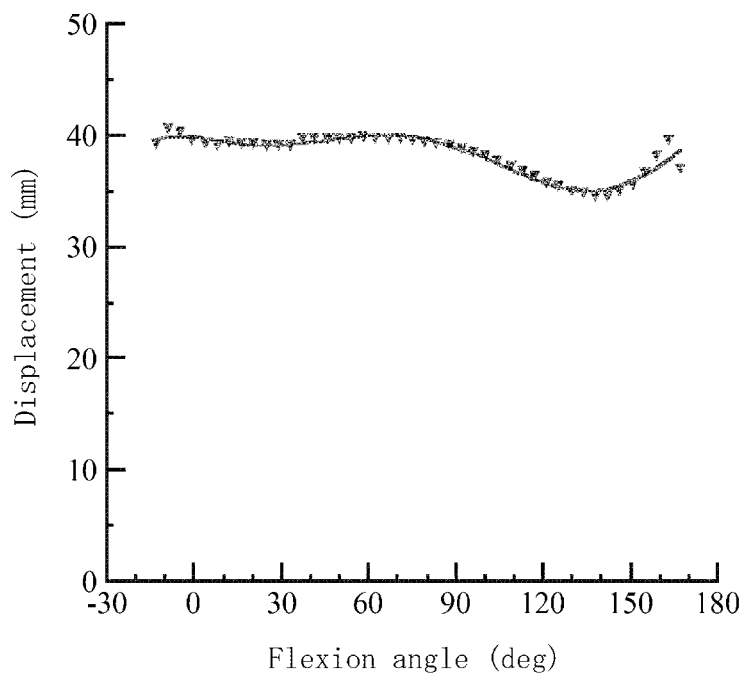
FIG. 24 is a view illustrating a relationship between the bending angle of the knee and the length of the ligament in the practical example.
Figure 24B:
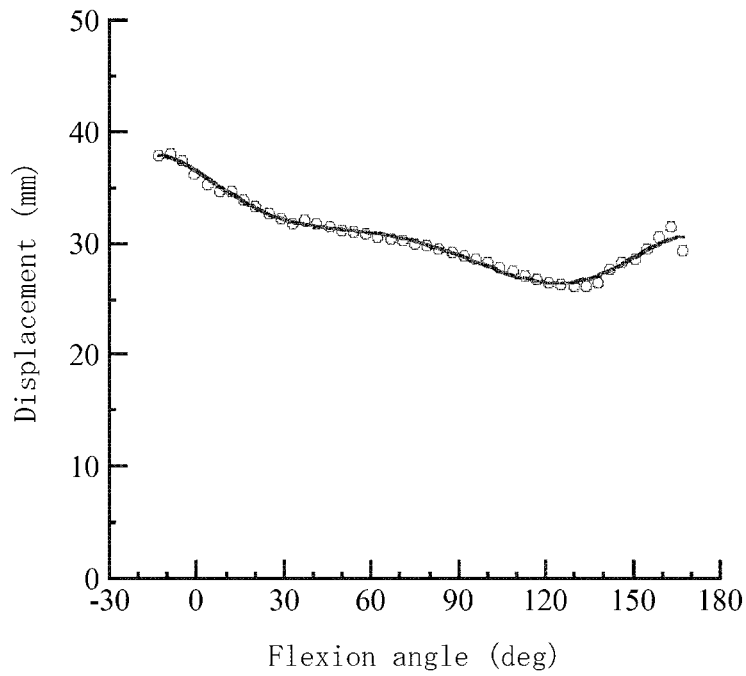
Figure 25A:
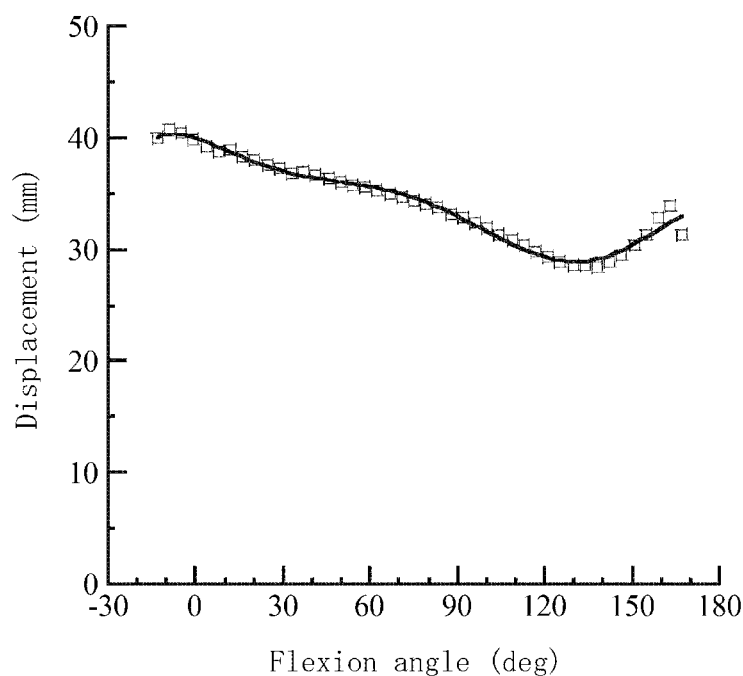
FIG. 25 is a view illustrating a relationship between the bending angle of the knee and the length of the ligament in the practical example.
Figure 25B:
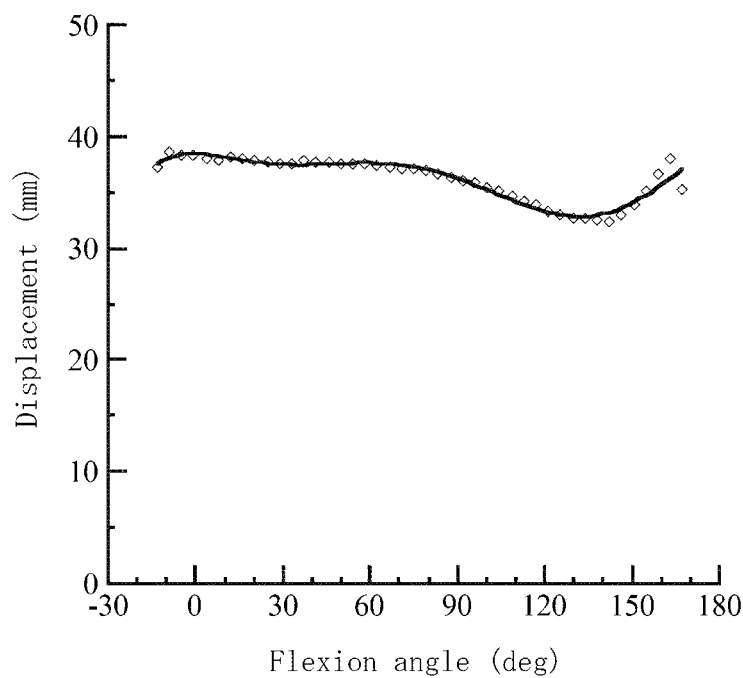
Figure 26A:
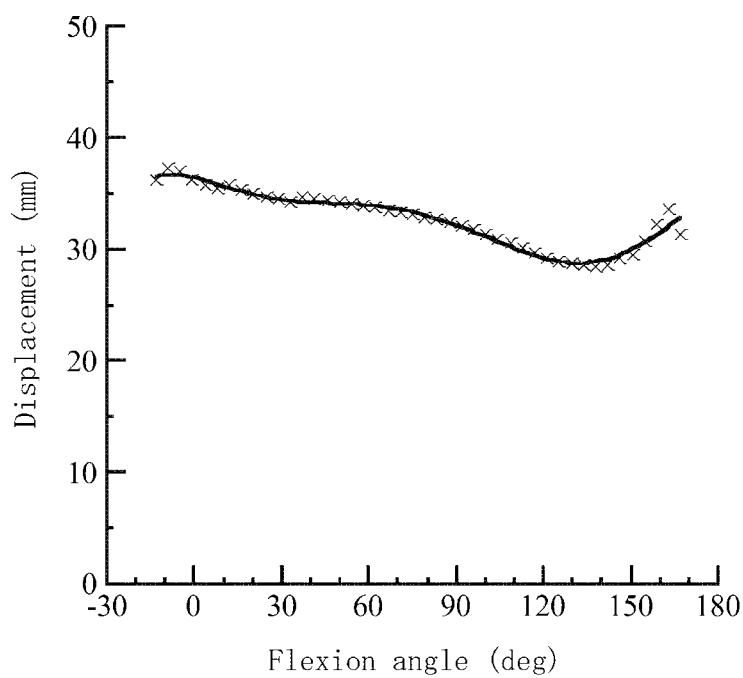
FIG. 26 is a view illustrating a relationship between the bending angle of the knee and the length of the ligament in the practical example.
Figure 26B:
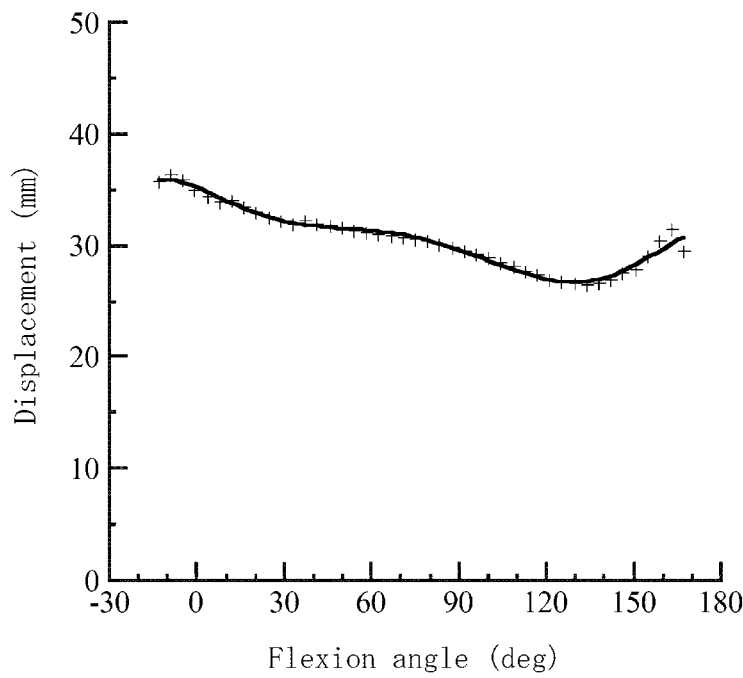
Figure 27A:
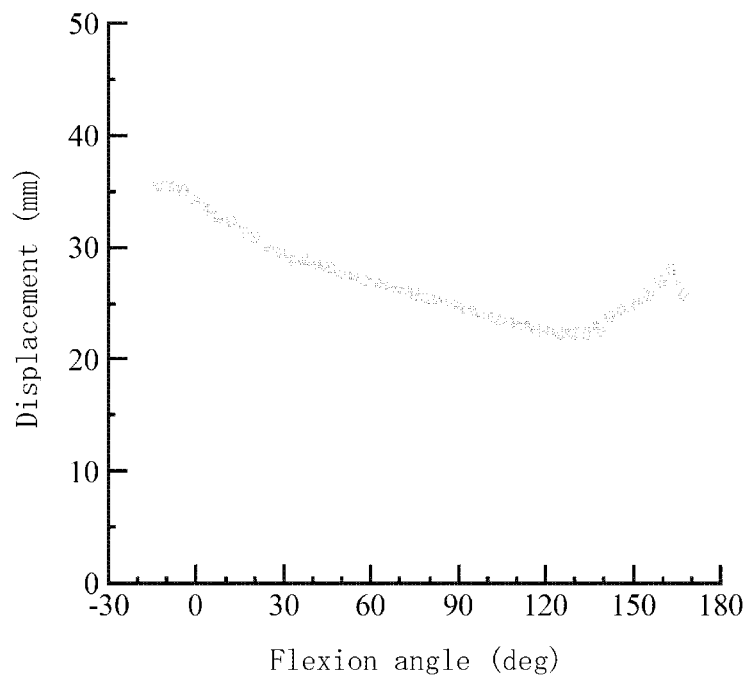
FIG. 27 is a view illustrating a relationship between the bending angle of the knee and the length of the ligament in the practical example.
Figure 27B:
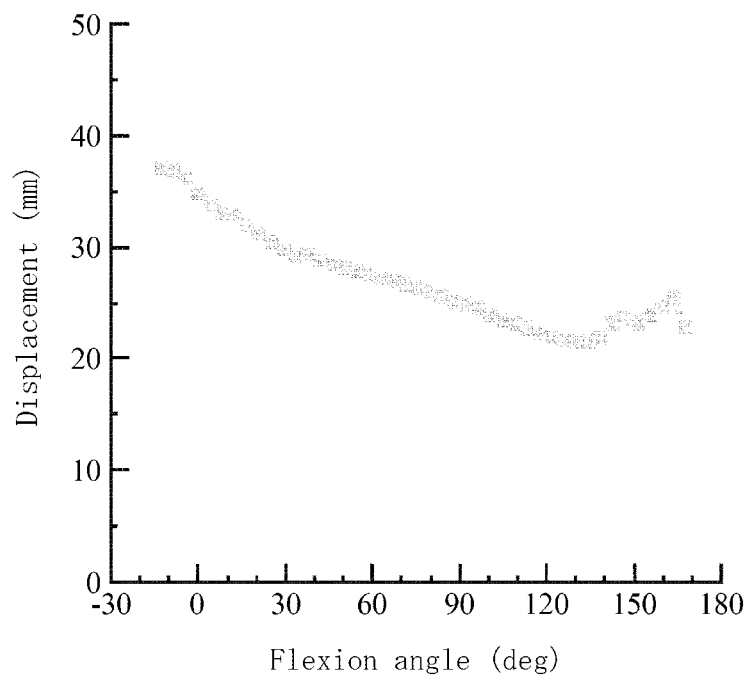
Figure 28A:
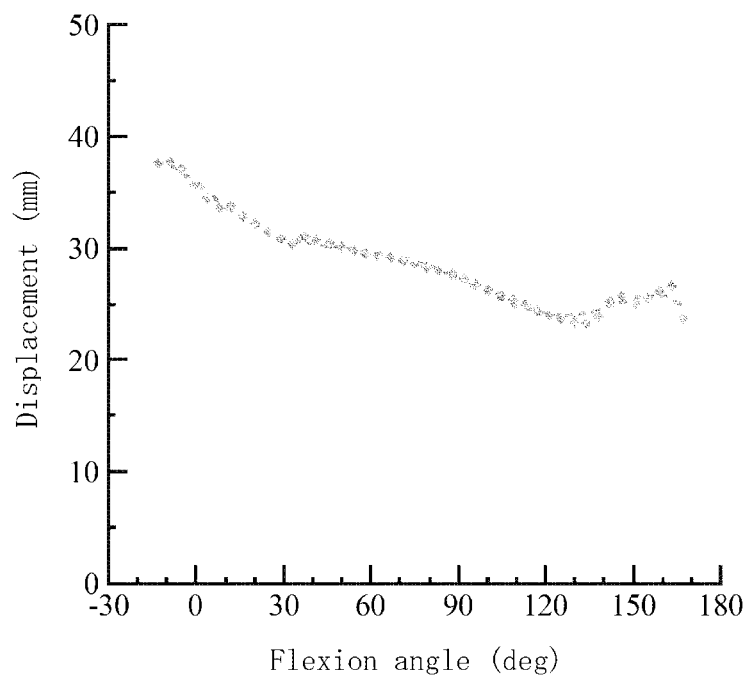
FIG. 28 is a view illustrating a relationship between the bending angle of the knee and the length of the ligament in the practical example.
Figure 28B:
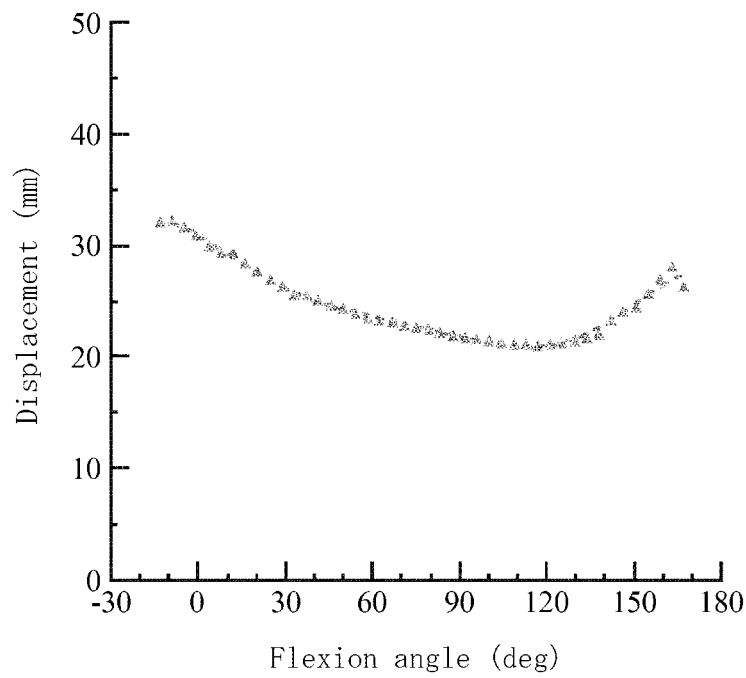
Figure 29A:
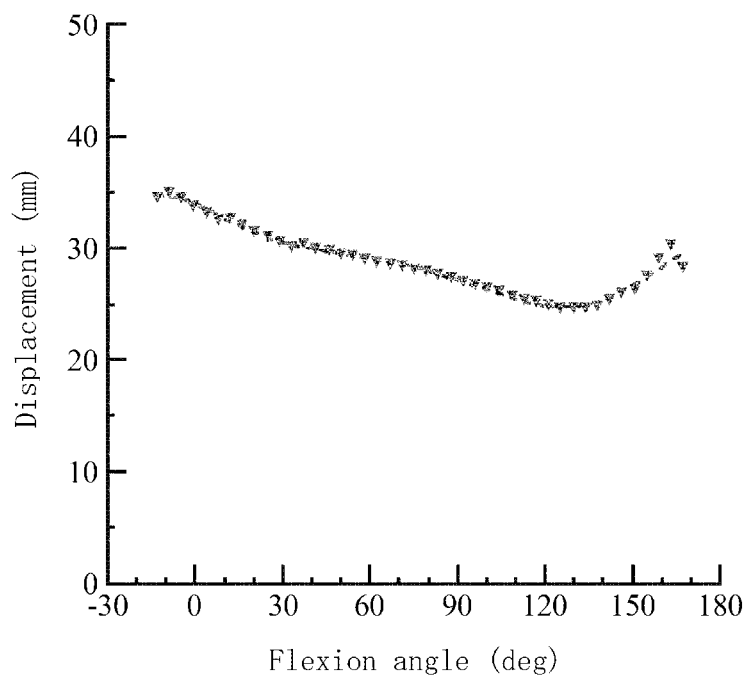
FIG. 29 is a view illustrating a relationship between the bending angle of the knee and the length of the ligament in the practical example.
Figure 29B:
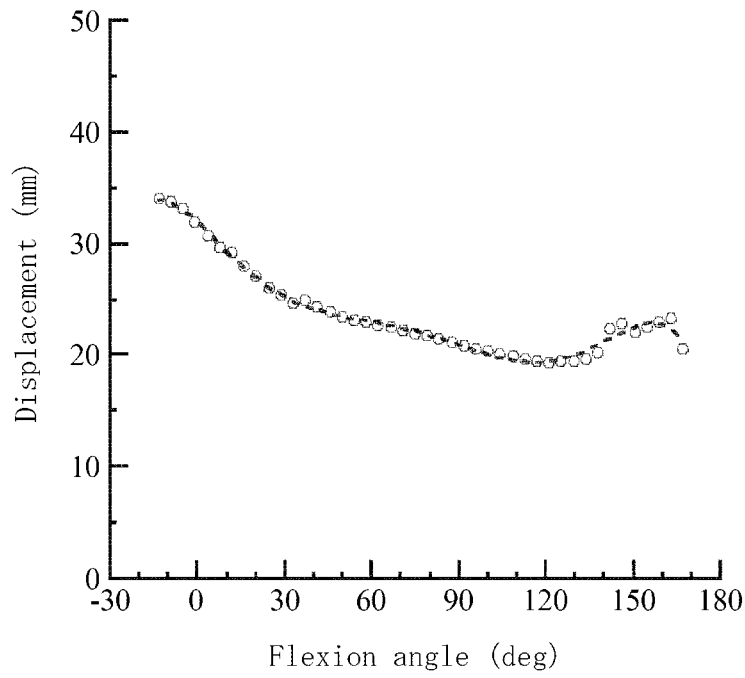
Figure 30A:
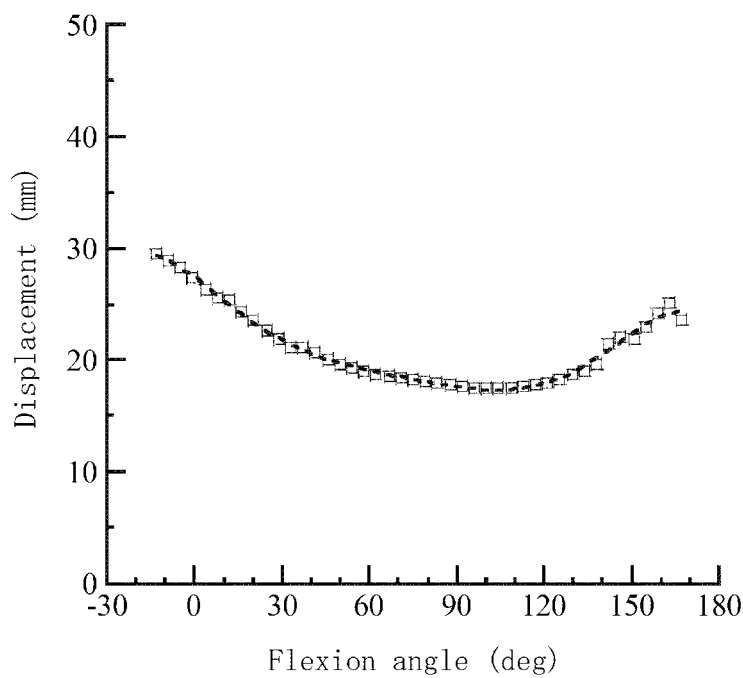
FIG. 30 is a view illustrating a relationship between the bending angle of the knee and the length of the ligament in the practical example.
Figure 30B:
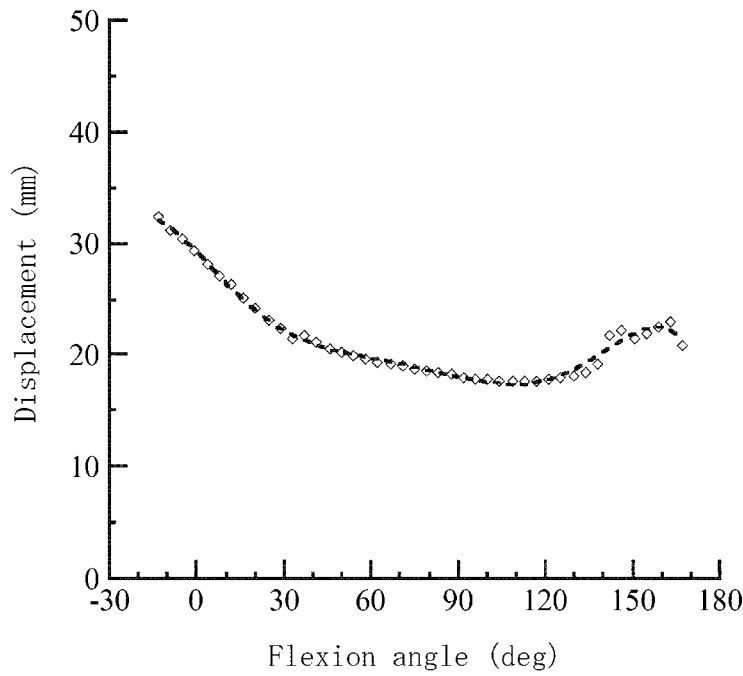
Figure 31A:
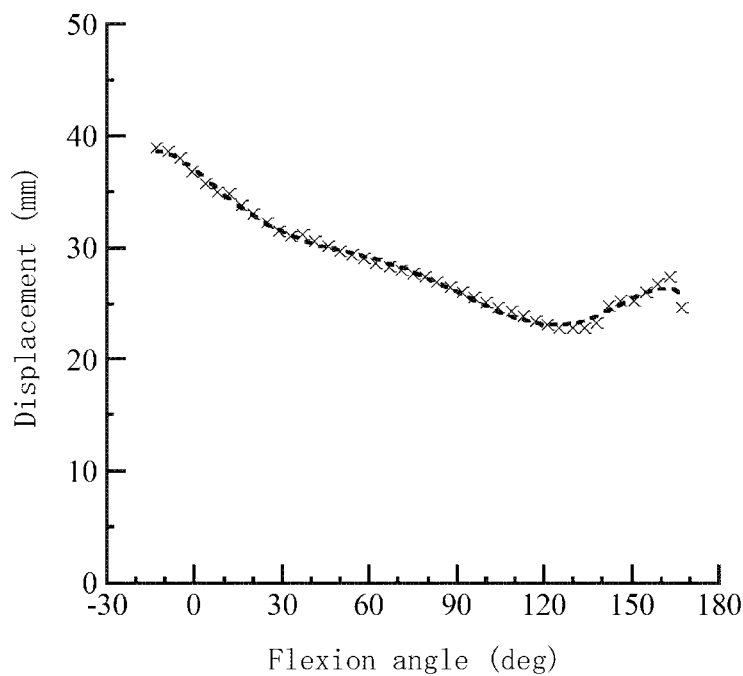
FIG. 31 is a view illustrating a relationship between the bending angle of the knee and the length of the ligament in the practical example.
Figure 31B:
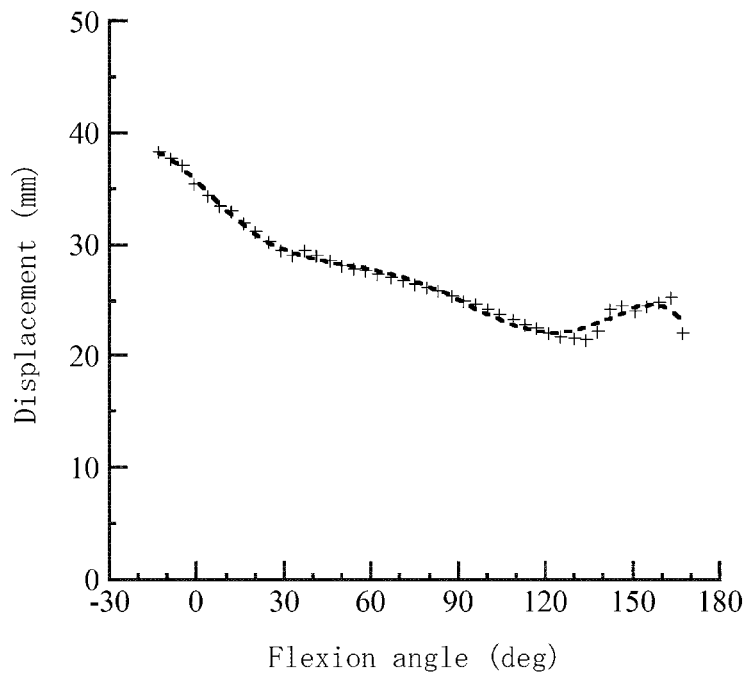

As illustrated in FIG. 21, in the practical example, it was checked that tendencies of the knee bending angle and the change in length of the anterior cruciate ligament indicated a tendency of the anterior cruciate ligament (DEFORT) of the normal knee, namely, it was checked that the reconstructed anterior cruciate ligament exerted the function equal to the anterior cruciate ligament of the human when the ligament insertion hole was formed in the tibia member like the practical example.

As illustrated in FIGS. 22 to 31, in each bundle, it can be checked that the bundle length changes according to the knee bending angle. It can be checked that the angles at which the tension and relief states are generated vary in each bundle. For example, in the bundles 1, 2, 4, 5, and 11, the state (tension state) in which the bundle length does not change is maintained until the knee is deeply bent. On the other hand, in the bundles 17, 18, 19, and 20, the relief state is generated at the position where the knee is shallowly bent, and the relief state progresses as the knee is deeply bent. That is, when the anterior cruciate ligament is regarded as one strip, it can be checked that the tension or relief state of the bundle changes variously according to the radial position or the angle about the center axis. Therefore, it was checked that the anterior cruciate ligament was brought into contact with the surface of the tibia member or femur to a certain degree to disperse various functions of the anterior cruciate ligament.

Figure 32:
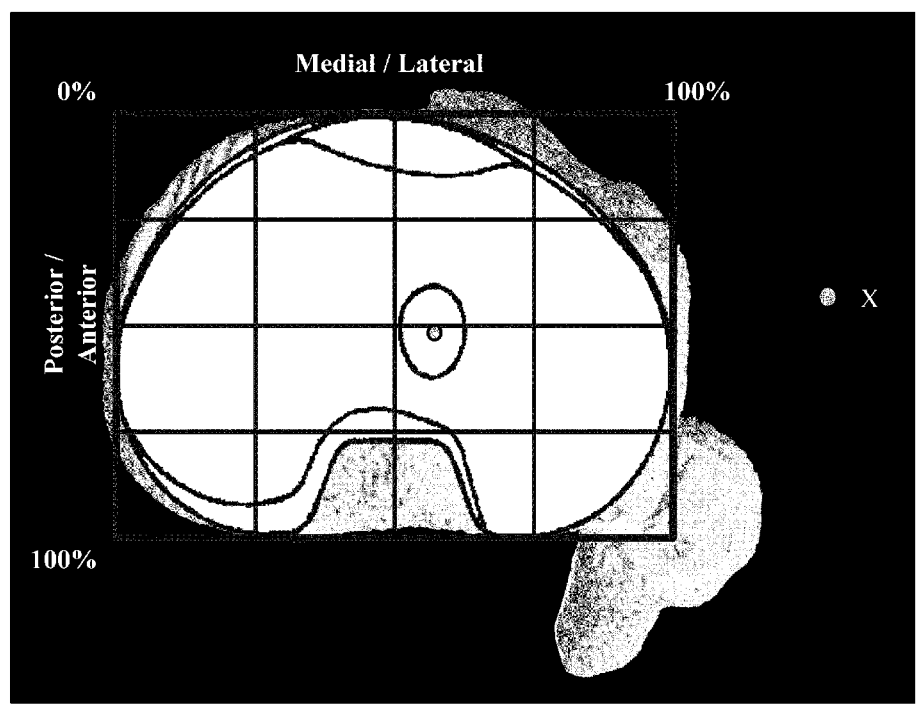
FIG. 32 is a view illustrating the joining position (ligament insertion hole) relationship between the anterior cruciate ligament and the tibia in a simulation of a comparative example.
Figure 33:
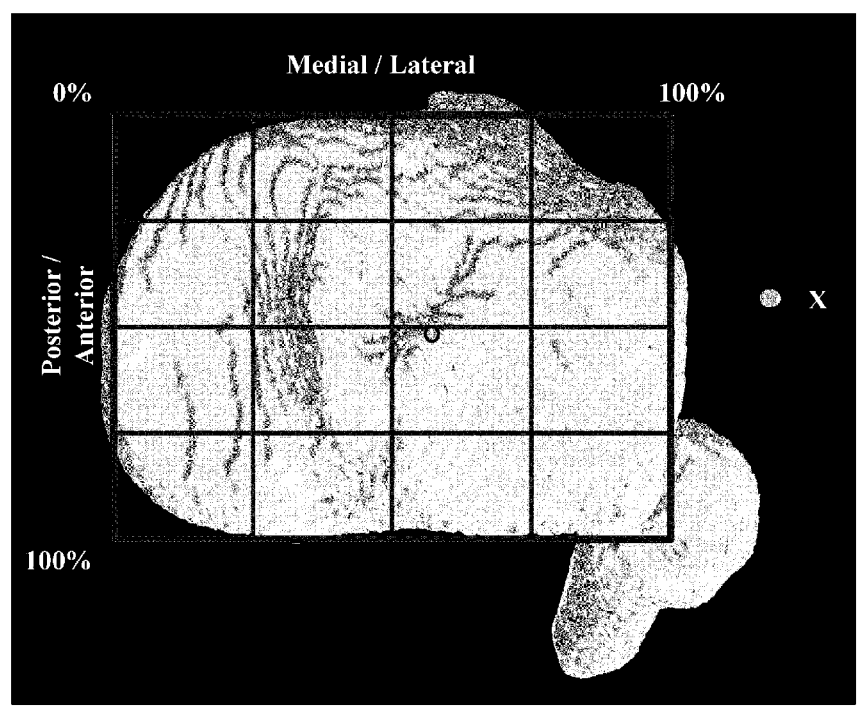
FIG. 33 is a view illustrating the joining position (ligament insertion hole) relationship between the anterior cruciate ligament and the tibia in the simulation of the comparative example.
Figure 34:
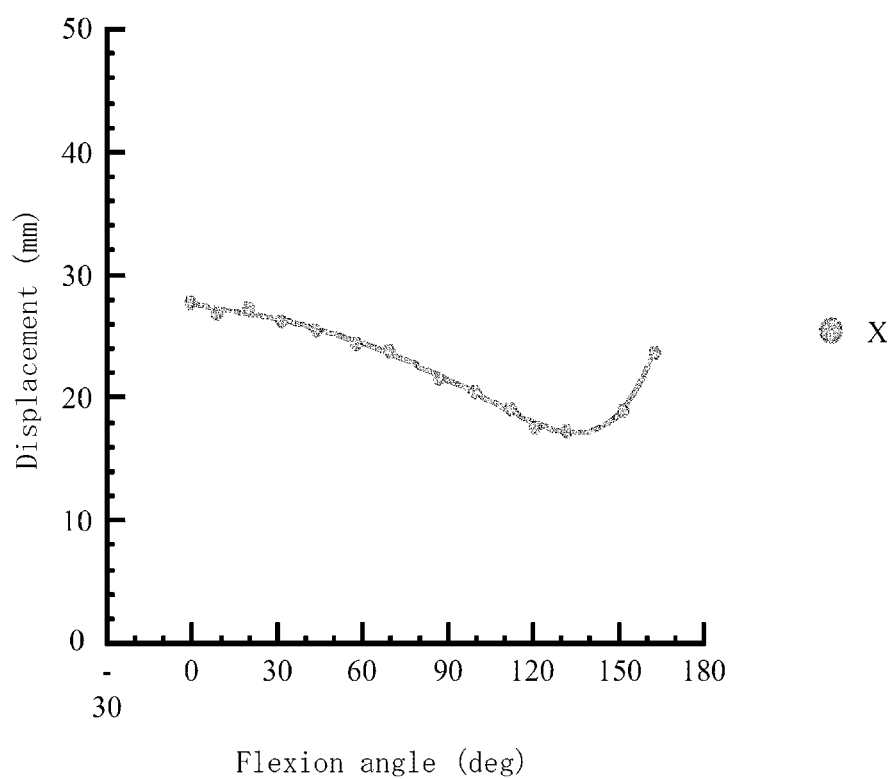
FIG. 34 is a view illustrating a relationship between the bending angle of the knee and the length of the anterior cruciate ligament in the comparative example.

On the other hand, the case that the ligament insertion hole was formed at the position (FIGS. 32 and 33) disclosed in Patent Document 5 in the tibia member was simulated as a comparative example. As illustrated in FIG. 34, in the comparative example, it was checked that the tendencies of the knee bending angle and the change in length of the anterior cruciate ligament was different from the tendency of the anterior cruciate ligament (DEFORT) of the human by increasing the knee bending angle. Because the position of the hole disclosed in Patent Document 5 differed from an originally anatomical position, it was checked that the anterior cruciate ligament took the extreme tension pattern. Therefore, it was clear that the tension pattern of the originally normal knee was hardly generated even if the hole was formed as disclosed in Patent Document 5. That is, it was checked that the reconstructed anterior cruciate ligament did not exert the sufficient function only by forming the hole through which the anterior cruciate ligament passes.

(Interference State Between Anterior Cruciate Ligament and Intercondylar Eminence)

In the practical example, how each bundle of reconstruction ligaments constituting the anterior cruciate ligament interfered with the intercondylar eminence in bending the knee was checked by the simulation. In the simulation, the state in which the bundle of reconstruction ligaments interfered with the intercondylar eminence was checked with respect to the case where the knee was bent at each of angles 112 degrees, 121 degrees, and 131 degrees.

Each bundle of reconstruction ligaments was connected to the tibia member and the femur at the positions in FIGS. 17 to 20.

Figure 35A:
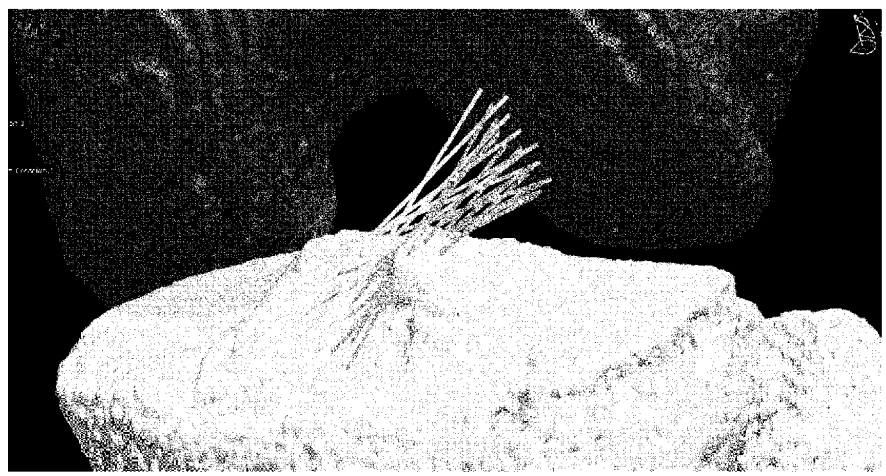
FIG. 35(A) is a view illustrating a result of a state in which the knee is bend at 112 degrees.
Figure 35B:
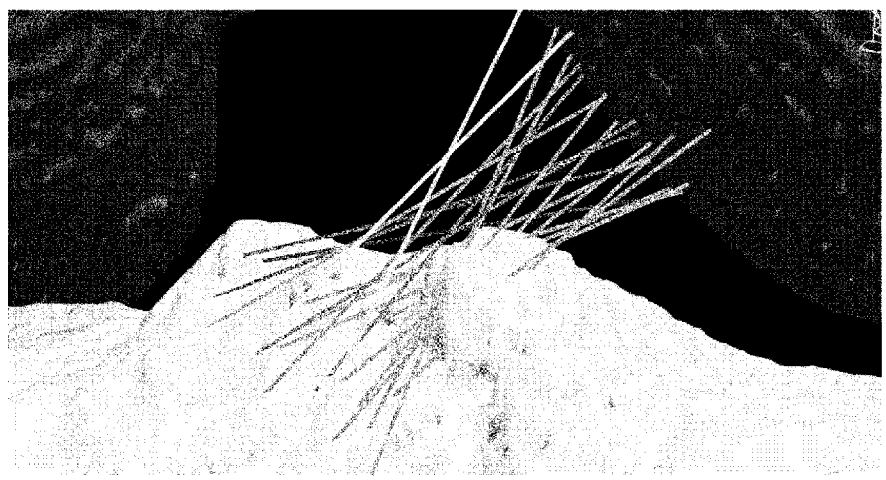
FIG. 35(B) is a view illustrating a result of a state in which the knee is bend at 121 degrees.
Figure 36A:
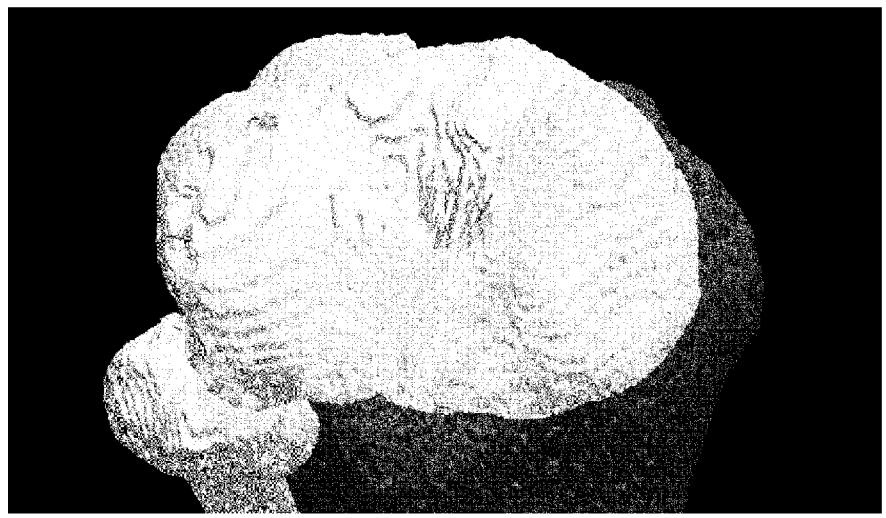
FIG. 36 is a view illustrating a relationship between the bending angle of the knee and the length of the anterior cruciate ligament in the comparative example.
Figure 36B:
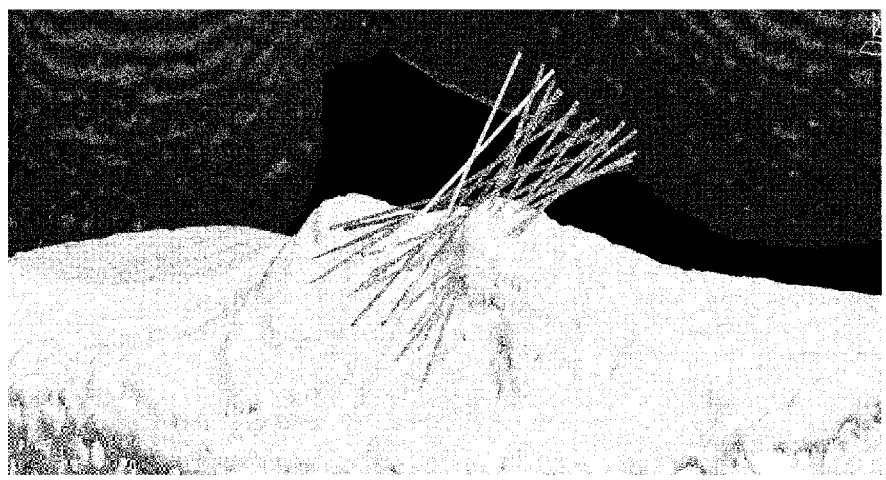

As illustrated in FIGS. 35 and 36, it was checked that, in the plural bundles of reconstruction ligaments constituting the anterior cruciate ligament, the bundle (PL group) located on the rear side interfered strongly with the intercondylar eminence by bending the knee while the bundle (AM group) located on the front side interfered weakly with the intercondylar eminence. It was checked that the interference was crowded as the knee was deeply bent, and that the tensile force closer to the organism anterior cruciate ligament was able to be generated when the anterior cruciate ligament was reconstructed using not one reconstruction ligament but the plural bundles of reconstruction ligaments.

INDUSTRIAL APPLICABILITY

The artificial knee joint of the present invention is suitable for the artificial knee joint used in the total knee replacement in the treatment of the knee osteoarthritis, the joint rheumatism, or the like.

DESCRIPTION OF REFERENCE SIGNS 1 artificial knee joint
10 femur member
11 medial condyle
12 lateral condyle
20 tibia member
20$h$ ligament insertion hole
21 medial condyle
22 lateral condyle
23 intercondylar eminence
F femur
DT distal end T tibia
PE proximal end
ACL anterior cruciate ligament
PCL posterior cruciate ligament

The invention claimed is:

1. An artificial knee joint that is used in a total knee replacement to join a femur and a tibia to each other using a reconstruction anterior cruciate ligament formed by a plurality of bundles of reconstruction ligaments, the artificial knee joint comprising:
 a femur member configured to be mounted on a distal end of the femur; and
 a tibia member comprising a base part configured to be mounted on a proximal end of the tibia,
 wherein
  a medial condyle and a lateral condyle are provided in the tibia member, the medial condyle and the lateral condyle of the tibia member are configured to be in direct contact with a medial condyle and a lateral condyle of the femur member, respectively,
  a ligament insertion hole piercing the tibia member and a prominence are provided between the medial condyle and the lateral condyle of the tibia member,
  the ligament insertion hole is a through-hole extending continuously and completely through both a top surface of the tibia member and the base part of the tibia member such that the ligament insertion hole is configured to receive the reconstruction anterior cruciate ligament in order to allow the reconstruction anterior cruciate ligament to extend through the ligament insertion hole,
  the prominence is formed between the ligament insertion hole and a notch provided in a rear portion of the tibia member,
  the prominence projects more towards the femur member than the medial condyle and the lateral condyle of the tibia member, and
  a recess extending anteroposteriorly along the artificial knee joint is provided at a tip of the prominence in order to generate an appropriate interference state for each of the bundles of the reconstruction ligaments of the reconstruction anterior cruciate ligament throughout knee flexion and extension.

2. The artificial knee joint according to claim 1, wherein the ligament insertion hole is provided such that a center of an opening of the ligament insertion hole is disposed at a position of 25% to 50% from a front end of the tibia member, and such that the center of the opening is disposed at a position of 0 to 10% from right to left from a center of the tibia member in right and left directions.

3. The artificial knee joint according to claim 1, wherein a plurality of ligament insertion holes are provided such that a center of an opening of each hole is disposed at a position of 25% to 50% from a front end of the tibia member, and such that the center of the opening of each hole is disposed at a position of 0 to 10% from right to left from a center of the tibia member in right and left directions.

4. The artificial knee joint according to claim 1, wherein in the tibia member,
 a central portion of the medial condyle is formed into a concave surface, and
 a central portion of the lateral condyle is formed into a flat surface.

5. The artificial knee joint according to claim 4, wherein in the tibia member, a surface connecting a front end and a rear end of the concave surface in the central portion of the medial condyle is formed so as to tilt backward with respect to the flat surface in the central portion of the lateral condyle in a side view.

6. The artificial knee joint according to claim 4, wherein in the tibia member, a surface of the medial condyle tilts inward so as to be lower than a surface in the central portion of the lateral condyle in a rear view.

7. The artificial knee joint according to claim 1, wherein, in the tibia member, peripheral portions of the medial condyle or the lateral condyle are formed into a curved shape.

8. The artificial knee joint according to claim 7, wherein, in the tibia member, a boundary portion between either a side surface or a rear surface and a peripheral portion of the lateral condyle is formed into an outward convex surface.

9. The artificial knee joint according to claim 7, wherein, in the tibia member, a first boundary portion between a side surface and a peripheral portion of the lateral condyle and a second boundary portion between a rear surface and the peripheral portion of the lateral condyle are both formed into outward convex surfaces.

10. The artificial knee joint according to claim 1, wherein, in the tibia member, peripheral portions of the medial condyle and peripheral portions of the lateral condyle are formed into a curved shape.

11. The artificial knee joint according to claim 1, further comprising the reconstruction anterior cruciate ligament, wherein the reconstruction anterior cruciate ligament is configured to be directly connected to the femur and the tibia.

12. The artificial knee joint according to claim 1, wherein the recess is positioned between the ligament insertion hole and the notch.

* * * * *